United States Patent
Flanagan et al.

(10) Patent No.: US 9,795,756 B2
(45) Date of Patent: *Oct. 24, 2017

(54) CANNULA FOR MINIMIZING DILUTION OF DOSING DURING NITRIC OXIDE DELIVERY

(71) Applicant: Mallinckrodt Hospital Products IP Limited, Mulhuddart, Dublin (IE)

(72) Inventors: Craig Flanagan, Belmar, NJ (US); Simon Freed, Providence, RI (US); John Klaus, Cottage Grove, WI (US); Thomas Kohlmann, McFarland, WI (US); Martin D. Meglasson, Bloomsbury, NJ (US); Manesh Naidu, Randolph, NJ (US); Parag Shah, Morristown, NJ (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 812 days.

This patent is subject to a terminal disclaimer.

(21) Appl. No.: 14/096,548

(22) Filed: Dec. 4, 2013

(65) Prior Publication Data

US 2014/0166009 A1 Jun. 19, 2014

Related U.S. Application Data

(60) Provisional application No. 61/733,134, filed on Dec. 4, 2012, provisional application No. 61/784,238, filed on Mar. 14, 2013.

(51) Int. Cl.
*A61M 16/06* (2006.01)
*A61M 16/20* (2006.01)
*A61M 16/08* (2006.01)

(52) U.S. Cl.
CPC ........ *A61M 16/0677* (2014.02); *A61M 16/06* (2013.01); *A61M 16/0666* (2013.01);
(Continued)

(58) Field of Classification Search
CPC .. A61M 16/00; A61M 16/06; A61M 16/0666; A61M 16/0672; A61M 16/0677;
(Continued)

(56) References Cited

U.S. PATENT DOCUMENTS

| 759,152 A | 5/1904 | Bennett |
| 1,369,631 A | 2/1921 | De Vilbiss |

(Continued)

FOREIGN PATENT DOCUMENTS

| WO | 89/09565 A1 | 10/1989 |
| WO | WO-2012/006415 | 1/2012 |
| WO | WO-2012/106373 | 8/2012 |

OTHER PUBLICATIONS

Non-Final Office Action in U.S. Appl. No. 14/096,629, dated Apr. 1, 2014, 12 pages.
(Continued)

*Primary Examiner* — Justine Yu
*Assistant Examiner* — Colin W Stuart
(74) *Attorney, Agent, or Firm* — Servilla Whitney LLC

(57) ABSTRACT

Described are nasal cannulas that improve the precision of the delivered dose for nitric oxide therapy by reducing the dilution of nitric oxide. The nasal cannulas may reduce the total volume and potential for retrograde flow during nitric oxide therapy through the design of the specific dimensions of the flow path and/or having check valves in the nitric oxide delivery line and/or having a flapper or umbrella valve dedicated to nitric oxide delivery. The nasal cannulas may also use materials that limit oxygen diffusion through the (Continued)

cannula walls. The nosepiece for these cannulas may be manufactured by a molding technique.

21 Claims, 20 Drawing Sheets

(52) U.S. Cl.
CPC ..... *A61M 16/0672* (2014.02); *A61M 16/0858* (2014.02); *A61M 16/208* (2013.01); *A61M 2202/0208* (2013.01); *A61M 2202/0275* (2013.01); *A61M 2206/10* (2013.01); *A61M 2207/00* (2013.01)

(58) Field of Classification Search
CPC .......... A61M 16/12; A61M 2202/0275; A61M 2210/0618
USPC .................................................. 128/207.18
See application file for complete search history.

(56) References Cited

U.S. PATENT DOCUMENTS

| | | |
|---|---|---|
| 1,443,820 A | 1/1923 | Hudson |
| 1,856,811 A | 5/1932 | Inaki |
| 2,860,634 A | 11/1958 | Duncan et al. |
| 2,931,358 A | 4/1960 | Sheridan |
| 3,260,258 A | 7/1966 | Berman |
| 3,513,844 A | 5/1970 | Smith |
| 3,682,171 A | 8/1972 | Dali et al. |
| 3,867,946 A | 2/1975 | Huddy |
| 3,877,436 A | 4/1975 | Havstad |
| 3,915,173 A | 10/1975 | Brekke |
| 3,951,175 A | 4/1976 | Eberhart |
| 3,972,321 A | 8/1976 | Proctor |
| 4,015,366 A | 4/1977 | Hall, III |
| 4,015,598 A | 4/1977 | Brown |
| 4,054,133 A | 10/1977 | Myers |
| 4,151,843 A | 5/1979 | Brekke et al. |
| 4,265,235 A | 5/1981 | Fukunaga |
| 4,280,493 A | 7/1981 | Council |
| 4,291,691 A | 9/1981 | Cabal et al. |
| 4,300,550 A | 11/1981 | Gandi et al. |
| 4,320,754 A | 3/1982 | Watson et al. |
| 4,333,451 A | 6/1982 | Paluch |
| RE31,023 E | 9/1982 | Hall, III |
| 4,363,323 A | 12/1982 | Geiss |
| 4,403,611 A | 9/1983 | Babbitt et al. |
| 4,462,397 A | 7/1984 | Suzuki |
| 4,465,067 A | 8/1984 | Koch et al. |
| 4,485,822 A | 12/1984 | O'Connor et al. |
| 4,517,404 A | 5/1985 | Hughes et al. |
| 4,521,038 A | 6/1985 | Cerny |
| 4,535,767 A | 8/1985 | Tiep et al. |
| 4,559,941 A | 12/1985 | Timmons et al. |
| 4,584,997 A | 4/1986 | Delong |
| 4,602,644 A | 7/1986 | DiBenedetto et al. |
| 4,634,425 A | 1/1987 | Meer |
| 4,648,398 A | 3/1987 | Agdanowski et al. |
| 4,660,555 A | 4/1987 | Payton |
| 4,699,139 A | 10/1987 | Marshall et al. |
| 4,778,448 A | 10/1988 | Meer |
| 4,790,832 A | 12/1988 | Lopez |
| 4,796,615 A | 1/1989 | Bullock et al. |
| 4,801,093 A | 1/1989 | Brunet et al. |
| 4,821,715 A | 4/1989 | Downing |
| 4,826,510 A | 5/1989 | McCombs |
| 4,829,998 A | 5/1989 | Jackson |
| 4,838,257 A | 6/1989 | Hatch |
| 4,893,620 A | 1/1990 | Wadwha |
| 4,949,716 A | 8/1990 | Chenoweth |
| 4,957,107 A | 9/1990 | Sipin |
| 4,989,599 A | 2/1991 | Carter |
| 4,996,983 A | 3/1991 | AmRhein |
| 5,011,474 A | 4/1991 | Brennan |
| 5,018,519 A | 5/1991 | Brown |
| 5,025,805 A | 6/1991 | Nutter |
| 5,027,809 A | 7/1991 | Robinson |
| 5,027,812 A | 7/1991 | Shapiro et al. |
| 5,046,491 A | 9/1991 | Derrick |
| 5,088,486 A | 2/1992 | Jinotti |
| 5,099,836 A | 3/1992 | Rowland et al. |
| 5,105,807 A | 4/1992 | Kahn et al. |
| 5,109,839 A | 5/1992 | Blasdell et al. |
| 5,117,818 A | 6/1992 | Palfy |
| 5,121,746 A | 6/1992 | Sikora |
| 5,140,983 A | 8/1992 | Jinotti |
| 5,222,486 A | 6/1993 | Vaughn |
| 5,243,971 A | 9/1993 | Sullivan |
| 5,269,296 A | 12/1993 | Landis |
| 5,291,897 A | 3/1994 | Gastrin et al. |
| 5,311,862 A | 5/1994 | Blasdell et al. |
| 5,331,954 A | 7/1994 | Rex et al. |
| 5,357,948 A | 10/1994 | Eilentripp |
| 5,400,776 A | 3/1995 | Bartholomew |
| 5,404,873 A | 4/1995 | Leagre et al. |
| 5,419,317 A | 5/1995 | Blasdell et al. |
| 5,429,127 A | 7/1995 | Kolobow |
| 5,437,267 A | 8/1995 | Weinstein et al. |
| 5,526,806 A | 6/1996 | Sansoni |
| 5,538,000 A | 7/1996 | Rudolph |
| 5,540,221 A | 7/1996 | Kaigler et al. |
| 5,599,304 A | 2/1997 | Shaari |
| 5,601,077 A | 2/1997 | Imbert |
| 5,603,315 A | 2/1997 | Sasso, Jr. |
| 5,605,149 A | 2/1997 | Warters |
| 5,626,130 A | 5/1997 | Vincent et al. |
| 5,632,268 A | 5/1997 | Ellis et al. |
| 5,640,951 A | 6/1997 | Huddart et al. |
| 5,664,567 A | 9/1997 | Linder |
| 5,676,137 A | 10/1997 | Byrd |
| 5,682,881 A | 11/1997 | Winthrop et al. |
| 5,683,361 A | 11/1997 | Elk et al. |
| 5,692,498 A | 12/1997 | Lurie et al. |
| 5,743,258 A | 4/1998 | Sato et al. |
| 5,752,506 A | 5/1998 | Richardson |
| 5,755,225 A | 5/1998 | Hutson |
| 5,787,879 A | 8/1998 | Gibson |
| 5,788,665 A | 8/1998 | Sekins |
| 5,803,078 A | 9/1998 | Brauner |
| 5,845,633 A | 12/1998 | Psaros |
| 5,862,802 A | 1/1999 | Bird |
| 5,873,359 A | 2/1999 | Zapol et al. |
| 5,893,361 A | 4/1999 | Hughes |
| 5,901,705 A | 5/1999 | Leagre |
| 5,928,190 A | 7/1999 | Davis |
| 5,947,119 A | 9/1999 | Reznick |
| 5,954,050 A | 9/1999 | Christopher |
| 5,989,217 A | 11/1999 | Ohki |
| 6,012,455 A | 1/2000 | Goldstein |
| 6,058,932 A | 5/2000 | Hughes |
| 6,067,984 A | 5/2000 | Piper |
| 6,119,693 A | 9/2000 | Kwok et al. |
| 6,142,147 A | 11/2000 | Head et al. |
| 6,152,132 A | 11/2000 | Psaros |
| 6,155,252 A | 12/2000 | Warters |
| 6,228,070 B1 | 5/2001 | Mezzoli |
| 6,247,470 B1 | 6/2001 | Ketchedjian |
| 6,267,114 B1 | 7/2001 | Ueno |
| 6,270,512 B1 | 8/2001 | Rittmann |
| 6,279,576 B1 | 8/2001 | Lambert |
| 6,283,123 B1 | 9/2001 | Van Meter et al. |
| 6,318,366 B1 | 11/2001 | Davenport |
| 6,378,520 B1 | 4/2002 | Davenport |
| 6,394,093 B1 | 5/2002 | Lethi |
| 6,394,142 B1 | 5/2002 | Woelfel et al. |
| 6,412,801 B1 | 7/2002 | Izuchukwu et al. |
| 6,422,240 B1 | 7/2002 | Levitsky et al. |
| 6,425,396 B1 | 7/2002 | Adriance et al. |
| 6,431,218 B1 | 8/2002 | Woelfel et al. |
| 6,439,230 B1 | 8/2002 | Gunaratnam et al. |
| 6,439,231 B1 | 8/2002 | Fukunaga et al. |
| 6,446,629 B1 | 9/2002 | Takaki et al. |
| 6,463,931 B1 | 10/2002 | Kwok et al. |

(56) References Cited

U.S. PATENT DOCUMENTS

| | | |
|---|---|---|
| 6,505,622 B2 | 1/2003 | Py |
| 6,505,624 B1 | 1/2003 | Campbell, Sr. |
| 6,520,931 B2 | 2/2003 | Suh |
| 6,536,436 B1 | 3/2003 | McGlothen |
| 6,540,718 B1 | 4/2003 | Wennek |
| 6,543,449 B1 | 4/2003 | Woodring et al. |
| 6,561,188 B1 | 5/2003 | Ellis |
| 6,561,193 B1 | 5/2003 | Noble |
| 6,564,799 B2 | 5/2003 | Fukunaga et al. |
| 6,571,794 B1 | 6/2003 | Hansen |
| 6,581,599 B1 | 6/2003 | Stenzler |
| 6,584,973 B1 | 7/2003 | Biondi et al. |
| 6,604,523 B2 | 8/2003 | Lurie |
| 6,631,717 B1 | 10/2003 | Rich |
| 6,655,385 B1 | 12/2003 | Curti et al. |
| 6,659,100 B2 | 12/2003 | O'Rourke |
| 6,668,828 B1 | 12/2003 | Figley et al. |
| 6,679,250 B2 | 1/2004 | Walker et al. |
| 6,681,764 B1 | 1/2004 | Honkonen et al. |
| 6,684,882 B1 | 2/2004 | Morine |
| 6,698,423 B1 | 3/2004 | Honkonen et al. |
| 6,772,761 B1 | 8/2004 | Rucker, Jr. |
| 6,776,162 B2 | 8/2004 | Wood |
| 6,776,163 B2 | 8/2004 | Dougill et al. |
| 6,789,543 B2 | 9/2004 | Cannon |
| 6,799,570 B2 | 10/2004 | Fisher et al. |
| 6,799,575 B1 | 10/2004 | Carter |
| 6,805,126 B2 | 10/2004 | Dutkiewicz |
| 6,828,577 B2 | 12/2004 | Zens |
| 6,849,049 B2 | 2/2005 | Starr et al. |
| 6,863,069 B2 | 3/2005 | Wood |
| 6,866,041 B2 | 3/2005 | Hardy, Jr. et al. |
| 6,874,500 B2 | 4/2005 | Fukunaga et al. |
| 6,880,557 B2 | 4/2005 | Downey |
| 6,886,561 B2 | 5/2005 | Bayron et al. |
| 6,889,688 B1 | 5/2005 | Wright |
| 6,899,102 B1 | 5/2005 | McGlothen |
| 6,901,927 B2 | 6/2005 | Deem et al. |
| 6,915,965 B2 | 7/2005 | Siebert |
| 6,938,619 B1 | 9/2005 | Hickle |
| 6,948,493 B2 | 9/2005 | Dunlop |
| 6,983,749 B2 | 1/2006 | Kumar |
| 6,994,089 B2 | 2/2006 | Wood |
| 6,997,918 B2 | 2/2006 | Soltesz et al. |
| 7,000,610 B2 | 2/2006 | Bennarsten et al. |
| 7,007,691 B2 | 3/2006 | Daugherty et al. |
| 7,007,694 B2 | 3/2006 | Aylsworth et al. |
| 7,011,094 B2 | 3/2006 | Rapacki et al. |
| 7,013,899 B2 | 3/2006 | Alfery et al. |
| 7,017,573 B1 | 3/2006 | Rasor et al. |
| 7,032,589 B2 | 4/2006 | Kerechanin, II et al. |
| 7,036,506 B2 | 5/2006 | McAuliffe et al. |
| 7,051,736 B2 | 5/2006 | Banner et al. |
| 7,059,328 B2 | 6/2006 | Wood |
| 7,066,174 B1 | 6/2006 | Smith et al. |
| 7,096,864 B1 | 8/2006 | Mayer et al. |
| 7,100,606 B2 | 9/2006 | Fisher et al. |
| 7,114,497 B2 | 10/2006 | Aylsworth et al. |
| 7,121,276 B2 | 10/2006 | Jagger et al. |
| 7,140,370 B2 | 11/2006 | Tresnak et al. |
| 7,146,976 B2 | 12/2006 | McKown |
| 7,152,604 B2 | 12/2006 | Hickle |
| 7,165,549 B2 | 1/2007 | Philipps et al. |
| 7,178,521 B2 | 2/2007 | Burrow et al. |
| 7,178,524 B2 | 2/2007 | Noble |
| 7,195,018 B1 | 3/2007 | Goldstein |
| 7,204,247 B1 | 4/2007 | Rogerson |
| 7,204,249 B1 | 4/2007 | Richey, II et al. |
| 7,204,251 B2 | 4/2007 | Lurie |
| 7,210,481 B1 | 5/2007 | Lovell et al. |
| 7,252,088 B1 | 8/2007 | Nieves-Ramirez |
| 7,261,105 B2 | 8/2007 | Fukunaga et al. |
| 7,273,050 B2 | 9/2007 | Wei |
| 7,275,541 B2 | 10/2007 | Fukunaga et al. |
| 7,278,420 B2 | 10/2007 | Ganesh et al. |
| 7,290,543 B2 | 11/2007 | Stradella |
| 7,318,437 B2 | 1/2008 | Gunaratnam et al. |
| 7,320,447 B1 | 1/2008 | Lynch |
| 7,328,703 B1 | 2/2008 | Tiep |
| 7,334,578 B2 | 2/2008 | Biondi et al. |
| 7,343,916 B2 | 3/2008 | Biondo et al. |
| 7,354,467 B2 | 4/2008 | Chen et al. |
| 7,383,839 B2 | 6/2008 | Porat et al. |
| 7,406,966 B2 | 8/2008 | Wondka |
| 7,418,965 B2 | 9/2008 | Fukunaga et al. |
| 7,428,902 B2 | 9/2008 | Du et al. |
| 7,434,578 B2 | 10/2008 | Dillard |
| 7,445,602 B2 | 11/2008 | Yamamori et al. |
| 7,461,649 B2 | 12/2008 | Gamard et al. |
| 7,461,656 B2 | 12/2008 | Gunaratnam et al. |
| 7,478,634 B2 | 1/2009 | Jam |
| 7,481,219 B2 | 1/2009 | Lewis et al. |
| 7,481,222 B2 | 1/2009 | Reissmann |
| 7,481,223 B1 | 1/2009 | Batistelli |
| 7,503,325 B2 | 3/2009 | Fuhrman et al. |
| 7,506,649 B2 | 3/2009 | Doshi et al. |
| 7,523,752 B2 | 4/2009 | Montgomery et al. |
| 7,527,053 B2 | 5/2009 | DeVries et al. |
| 7,533,670 B1 | 5/2009 | Freitag et al. |
| 7,552,728 B2 | 6/2009 | Bonney et al. |
| 7,578,294 B2 | 8/2009 | Pierro et al. |
| 7,600,511 B2 | 10/2009 | Power et al. |
| 7,617,824 B2 | 11/2009 | Doyle |
| 7,631,668 B2 | 12/2009 | Rantalainen |
| 7,655,063 B2 | 2/2010 | Wang et al. |
| 7,658,189 B2 | 2/2010 | Davidson et al. |
| 7,708,016 B2 | 5/2010 | Zaiser et al. |
| 7,708,017 B2 | 5/2010 | Davidson et al. |
| 7,717,109 B2 | 5/2010 | Fukunaga et al. |
| 7,717,116 B2 | 5/2010 | Mijers |
| 7,727,194 B2 | 6/2010 | Nalagatla et al. |
| 7,735,490 B2 | 6/2010 | Rinaldi |
| 7,735,491 B2 | 6/2010 | Doshi et al. |
| 7,740,014 B2 | 6/2010 | Djupesland |
| 7,743,767 B2 | 6/2010 | Ging et al. |
| 7,762,253 B2 | 7/2010 | Acker et al. |
| 7,775,210 B2 | 8/2010 | Schobel (nee Bauer) et al. |
| 7,779,841 B2 | 8/2010 | Dunsmore et al. |
| 7,798,148 B2 | 9/2010 | Doshi et al. |
| 7,806,120 B2 | 10/2010 | Loomas et al. |
| 7,832,400 B2 | 11/2010 | Curti et al. |
| 7,837,651 B2 | 11/2010 | Bishop et al. |
| 7,854,228 B2 | 12/2010 | Wilson et al. |
| 7,856,979 B2 | 12/2010 | Doshi et al. |
| 7,856,981 B2 | 12/2010 | McAuley et al. |
| 7,866,320 B2 | 1/2011 | Nichols |
| 7,870,857 B2 | 1/2011 | Chuper et al. |
| 7,874,291 B2 | 1/2011 | Ging et al. |
| 7,874,293 B2 | 1/2011 | Gunaratnam et al. |
| 7,900,635 B2 | 3/2011 | Gunaratnam et al. |
| 7,905,232 B2 | 3/2011 | Olsen et al. |
| 7,918,224 B2 | 4/2011 | Dolezal et al. |
| 7,918,225 B2 | 4/2011 | Dolezal et al. |
| 7,918,227 B1 | 4/2011 | Phythyon |
| 7,926,484 B2 | 4/2011 | Dhuper et al. |
| 7,942,148 B2 | 5/2011 | Davidson et al. |
| 7,942,150 B2 | 5/2011 | Guney et al. |
| 7,946,288 B2 | 5/2011 | Flynn et al. |
| 7,970,631 B2 | 6/2011 | Bruggeman et al. |
| 7,985,254 B2 | 7/2011 | Tolkowsky |
| 7,987,847 B2 | 8/2011 | Wickham et al. |
| 7,987,852 B2 | 8/2011 | Doshi et al. |
| 7,992,561 B2 | 8/2011 | Baker, Jr. et al. |
| 7,997,266 B2 | 8/2011 | Frazier et al. |
| 7,997,267 B2 | 8/2011 | Ging et al. |
| 7,997,271 B2 | 8/2011 | Hickle et al. |
| 8,015,974 B2 | 9/2011 | Christopher et al. |
| 8,020,556 B2 | 9/2011 | Hayek |
| 8,020,558 B2 | 9/2011 | Christopher et al. |
| 8,025,054 B2 | 9/2011 | Dunsmore et al. |
| 8,025,055 B1 | 9/2011 | Grady |
| 8,025,059 B2 | 9/2011 | Reissmann |
| 8,025,635 B2 | 9/2011 | Eaton et al. |
| 8,028,697 B2 | 10/2011 | Grychowski et al. |

(56) References Cited

U.S. PATENT DOCUMENTS

| | | |
|---|---|---|
| 8,042,536 B1 | 10/2011 | Howey |
| 8,042,542 B2 | 10/2011 | Ging et al. |
| 8,042,546 B2 | 10/2011 | Gunaratnam et al. |
| 8,061,357 B2 | 11/2011 | Pierce et al. |
| 8,080,000 B2 | 12/2011 | Makower et al. |
| 8,090,433 B2 | 1/2012 | Makower et al. |
| 8,113,198 B2 | 2/2012 | Teetzel et al. |
| 8,136,527 B2 | 3/2012 | Wondka |
| 8,146,591 B2 | 4/2012 | Niklewski et al. |
| 8,146,592 B2 | 4/2012 | Voege et al. |
| 8,151,790 B2 | 4/2012 | Lurie et al. |
| 8,161,971 B2 | 4/2012 | Jaffe et al. |
| RE43,398 E | 5/2012 | Honkonen et al. |
| 8,171,935 B2 | 5/2012 | Cortez, Jr. et al. |
| 8,177,805 B2 | 5/2012 | Alferness |
| 8,181,646 B2 | 5/2012 | Dhuper et al. |
| 8,186,352 B2 | 5/2012 | Gunaratnam et al. |
| 8,191,551 B2 | 6/2012 | Skovgard |
| 8,196,579 B2 | 6/2012 | Richards et al. |
| 8,196,582 B2 | 6/2012 | Ogilvie |
| 8,215,301 B2 | 7/2012 | Richards et al. |
| 8,220,463 B2 | 7/2012 | White et al. |
| 8,225,796 B2 | 7/2012 | Davenport et al. |
| 8,230,859 B1 | 7/2012 | Voege et al. |
| 8,245,710 B2 | 8/2012 | Makinson et al. |
| 8,267,083 B1 | 9/2012 | Goldstein et al. |
| 8,267,087 B2 | 9/2012 | Wruck et al. |
| 8,272,378 B2 | 9/2012 | Tutsch et al. |
| 8,281,557 B2 | 10/2012 | Doshi et al. |
| 8,286,636 B2 | 10/2012 | Gunaratnam et al. |
| 8,297,285 B2 | 10/2012 | Henry et al. |
| 8,302,603 B1 | 11/2012 | Weber |
| 8,302,606 B2 | 11/2012 | Doshi et al. |
| 8,302,607 B2 | 11/2012 | Pierce et al. |
| 8,307,829 B2 | 11/2012 | Brewer et al. |
| 8,312,881 B2 | 11/2012 | Gunaratnam et al. |
| 8,312,883 B2 | 11/2012 | Gunaratnam et al. |
| 8,316,851 B2 | 11/2012 | Wruck et al. |
| 8,333,194 B2 | 12/2012 | Lewis et al. |
| 8,333,199 B2 | 12/2012 | Landis et al. |
| 8,333,200 B2 | 12/2012 | Tero |
| 8,336,545 B2 | 12/2012 | Fink et al. |
| 8,337,454 B2 | 12/2012 | Eaton |
| RE43,886 E | 1/2013 | Mijers |
| 8,342,182 B2 | 1/2013 | Nair et al. |
| 8,347,881 B2 | 1/2013 | Tanaka et al. |
| 8,347,883 B2 | 1/2013 | Bird |
| 8,348,854 B2 | 1/2013 | Girshin |
| 8,356,595 B2 | 1/2013 | Schaeffer, Jr. et al. |
| 8,371,297 B2 | 2/2013 | Carey et al. |
| 8,371,302 B2 | 2/2013 | Ging et al. |
| 8,371,303 B2 | 2/2013 | Schaner et al. |
| 8,375,952 B2 | 2/2013 | Miller et al. |
| 8,387,616 B2 | 3/2013 | Ging et al. |
| 8,402,970 B2 | 3/2013 | Levi et al. |
| 8,408,204 B2 | 4/2013 | Lurie |
| 8,408,206 B2 | 4/2013 | Montgomery et al. |
| 8,409,168 B2 | 4/2013 | Wondka et al. |
| 8,424,529 B2 | 4/2013 | Efrati et al. |
| 8,424,530 B2 | 4/2013 | Gunaratnam et al. |
| 8,439,034 B2 | 5/2013 | Decker et al. |
| 8,443,802 B2 | 5/2013 | Schaeffer, Jr. et al. |
| 8,448,639 B2 | 5/2013 | Richards et al. |
| 8,469,025 B2 | 6/2013 | Mayer et al. |
| 8,469,027 B2 | 6/2013 | Choncholas |
| 8,474,449 B2 | 7/2013 | Tanaka |
| 8,475,369 B2 | 7/2013 | Boatner et al. |
| 8,486,043 B2 | 7/2013 | Iyer et al. |
| 8,522,782 B2 | 9/2013 | Lewis et al. |
| 8,534,278 B2 | 9/2013 | Colman et al. |
| 8,534,286 B2 | 9/2013 | Pierro et al. |
| 8,555,877 B2 | 10/2013 | Djupesland |
| 8,555,887 B2 | 10/2013 | Lisogurski |
| 8,561,607 B2 | 10/2013 | Cortez, Jr. et al. |
| 8,770,199 B2 | 7/2014 | Flanagan et al. |
| 9,032,959 B2 | 5/2015 | Flanagan et al. |
| 2001/0037808 A1 | 11/2001 | Deem et al. |
| 2001/0047804 A1 | 12/2001 | Fukunaga |
| 2002/0017302 A1 | 2/2002 | Fukunaga et al. |
| 2002/0046755 A1 | 4/2002 | De Voss |
| 2002/0054422 A1 | 5/2002 | Smith et al. |
| 2002/0055685 A1 | 5/2002 | Levitsky et al. |
| 2002/0069878 A1 | 6/2002 | Lurie et al. |
| 2002/0092527 A1 | 7/2002 | Wood |
| 2002/0108610 A1 | 8/2002 | Christopher |
| 2002/0112730 A1 | 8/2002 | Dutkiewicz |
| 2002/0121278 A1 | 9/2002 | Hete et al. |
| 2002/0148464 A1 | 10/2002 | Hoenig |
| 2002/0185126 A1 | 12/2002 | Krebs |
| 2003/0075176 A1 | 4/2003 | Fukunaga et al. |
| 2003/0079750 A1 | 5/2003 | Berthon-Jones |
| 2003/0116163 A1 | 6/2003 | Wood |
| 2003/0131844 A1 | 7/2003 | Kumar et al. |
| 2003/0131848 A1 | 7/2003 | Stenzler |
| 2003/0154979 A1 | 8/2003 | Berthon-Jones |
| 2003/0168058 A1 | 9/2003 | Walker et al. |
| 2003/0168067 A1 | 9/2003 | Dougill et al. |
| 2003/0172929 A1 | 9/2003 | Muellner |
| 2003/0172936 A1 | 9/2003 | Wilkie et al. |
| 2003/0183231 A1 | 10/2003 | Pedulla et al. |
| 2003/0183232 A1 | 10/2003 | Fukunaga et al. |
| 2003/0209246 A1 | 11/2003 | Schroeder et al. |
| 2003/0213493 A1 | 11/2003 | Saad |
| 2004/0000306 A1 | 1/2004 | Stradella |
| 2004/0000314 A1 | 1/2004 | Angel |
| 2004/0069304 A1 | 4/2004 | Jam |
| 2004/0069309 A1 | 4/2004 | Kirn |
| 2004/0103899 A1 | 6/2004 | Noble |
| 2004/0112378 A1 | 6/2004 | Djupesland |
| 2004/0112379 A1 | 6/2004 | Djupesland |
| 2004/0112380 A1 | 6/2004 | Djupesland |
| 2004/0129270 A1 | 7/2004 | Fishman |
| 2004/0134498 A1 | 7/2004 | Strickland et al. |
| 2004/0139973 A1 | 7/2004 | Wright |
| 2004/0149289 A1 | 8/2004 | Djupesland |
| 2004/0163647 A1 | 8/2004 | Figley et al. |
| 2004/0173212 A1 | 9/2004 | Berthon-Jones |
| 2004/0182397 A1 | 9/2004 | Wood |
| 2004/0194781 A1 | 10/2004 | Fukunaga et al. |
| 2004/0206354 A1 | 10/2004 | Fisher et al. |
| 2004/0216740 A1 | 11/2004 | Remmers et al. |
| 2004/0221845 A1 | 11/2004 | Pranger et al. |
| 2004/0221846 A1 | 11/2004 | Curti et al. |
| 2004/0226566 A1 | 11/2004 | Gunaratnam et al. |
| 2004/0231675 A1 | 11/2004 | Lyons |
| 2004/0244802 A1 | 12/2004 | Tanaka |
| 2004/0244804 A1 | 12/2004 | Olsen et al. |
| 2005/0005936 A1 | 1/2005 | Wondka |
| 2005/0011524 A1 | 1/2005 | Thomlinson et al. |
| 2005/0022828 A1 | 2/2005 | Fukunaga et al. |
| 2005/0028816 A1 | 2/2005 | Fishman et al. |
| 2005/0028823 A1 | 2/2005 | Wood |
| 2005/0034726 A1 | 2/2005 | Pittaway et al. |
| 2005/0039747 A1 | 2/2005 | Fukunaga et al. |
| 2005/0051163 A1 | 3/2005 | Deem et al. |
| 2005/0051176 A1 | 3/2005 | Riggins |
| 2005/0066973 A1 | 3/2005 | Michaels |
| 2005/0072430 A1 | 4/2005 | Djupesland |
| 2005/0103340 A1 | 5/2005 | Wondka |
| 2005/0103346 A1 | 5/2005 | Noble |
| 2005/0103347 A1 | 5/2005 | Curti et al. |
| 2005/0121033 A1 | 6/2005 | Starr et al. |
| 2005/0137715 A1 | 6/2005 | Phan et al. |
| 2005/0150501 A1 | 7/2005 | Opitz |
| 2005/0161049 A1 | 7/2005 | Wright |
| 2005/0166927 A1 | 8/2005 | McAuley et al. |
| 2005/0188990 A1 | 9/2005 | Fukunaga et al. |
| 2005/0199237 A1 | 9/2005 | Lurie |
| 2005/0205098 A1 | 9/2005 | Lampotang et al. |
| 2005/0217671 A1 | 10/2005 | Fisher et al. |
| 2005/0236000 A1 | 10/2005 | Wood |
| 2005/0252515 A1 | 11/2005 | Wood |
| 2005/0257794 A1 | 11/2005 | Aylsworth et al. |
| 2006/0011198 A1 | 1/2006 | Matarasso |

(56) References Cited

U.S. PATENT DOCUMENTS

| | | |
|---|---|---|
| 2006/0042631 A1 | 3/2006 | Martin et al. |
| 2006/0042632 A1 | 3/2006 | Bishop et al. |
| 2006/0042634 A1 | 3/2006 | Nalagatla et al. |
| 2006/0042636 A1 | 3/2006 | Nalagatla et al. |
| 2006/0042637 A1 | 3/2006 | Martin et al. |
| 2006/0042638 A1 | 3/2006 | Niklewski et al. |
| 2006/0060204 A1 | 3/2006 | Fuentes |
| 2006/0081257 A1 | 4/2006 | Krogh et al. |
| 2006/0107957 A1 | 5/2006 | Djupesland |
| 2006/0130840 A1 | 6/2006 | Porat et al. |
| 2006/0144401 A1 | 7/2006 | Boelt |
| 2006/0150979 A1 | 7/2006 | Doshi et al. |
| 2006/0150982 A1 | 7/2006 | Wood |
| 2006/0169281 A1 | 8/2006 | Aylsworth et al. |
| 2006/0174886 A1 | 8/2006 | Curti et al. |
| 2006/0174888 A1 | 8/2006 | Aylsworth et al. |
| 2006/0196502 A1 | 9/2006 | Pilcher et al. |
| 2006/0201512 A1 | 9/2006 | Garrett et al. |
| 2006/0207596 A1 | 9/2006 | Lane |
| 2006/0243278 A1 | 11/2006 | Hamilton et al. |
| 2006/0272645 A1 | 12/2006 | Ging et al. |
| 2007/0062538 A1 | 3/2007 | Foggia et al. |
| 2007/0062539 A1 | 3/2007 | Gunaratnam et al. |
| 2007/0068521 A1 | 3/2007 | Wang et al. |
| 2007/0107728 A1 | 5/2007 | Ricciardelli et al. |
| 2007/0107737 A1 | 5/2007 | Landis et al. |
| 2007/0113847 A1 | 5/2007 | Acker et al. |
| 2007/0113848 A1 | 5/2007 | Acker et al. |
| 2007/0113850 A1 | 5/2007 | Acker et al. |
| 2007/0113856 A1 | 5/2007 | Acker et al. |
| 2007/0119451 A1 | 5/2007 | Wang et al. |
| 2007/0137644 A1 | 6/2007 | Dhuper et al. |
| 2007/0163588 A1 | 7/2007 | Hebrank et al. |
| 2007/0175473 A1 | 8/2007 | Lewis et al. |
| 2007/0186928 A1 | 8/2007 | Be'eri |
| 2007/0186930 A1 | 8/2007 | Davidson et al. |
| 2007/0193580 A1 | 8/2007 | Feldhahn et al. |
| 2007/0199566 A1 | 8/2007 | Be'eri |
| 2007/0199568 A1 | 8/2007 | Diekens et al. |
| 2007/0233012 A1 | 10/2007 | Lerrick et al. |
| 2007/0256690 A1 | 11/2007 | Faram |
| 2007/0267025 A1 | 11/2007 | Lyons et al. |
| 2007/0277823 A1 | 12/2007 | Al-Ali et al. |
| 2007/0277832 A1 | 12/2007 | Doshi et al. |
| 2007/0283957 A1 | 12/2007 | Schobel (nee Bauer) et al. |
| 2008/0041373 A1 | 2/2008 | Doshi et al. |
| 2008/0041393 A1 | 2/2008 | Bracken |
| 2008/0051674 A1 | 2/2008 | Davenport et al. |
| 2008/0053458 A1 | 3/2008 | De Silva et al. |
| 2008/0060649 A1 | 3/2008 | Veliss et al. |
| 2008/0078388 A1 | 4/2008 | Vandine |
| 2008/0078393 A1 | 4/2008 | Acker et al. |
| 2008/0092891 A1 | 4/2008 | Cewers |
| 2008/0092906 A1 | 4/2008 | Gunaratnam et al. |
| 2008/0110451 A1 | 5/2008 | Dunsmore et al. |
| 2008/0110455 A1 | 5/2008 | Dunsmore et al. |
| 2008/0115787 A1 | 5/2008 | Ingenito |
| 2008/0121230 A1 | 5/2008 | Cortez et al. |
| 2008/0142003 A1 | 6/2008 | Depel |
| 2008/0142012 A1 | 6/2008 | Farnsworth et al. |
| 2008/0142018 A1 | 6/2008 | Doshi et al. |
| 2008/0142019 A1 | 6/2008 | Lewis et al. |
| 2008/0167603 A1 | 7/2008 | Stenzler et al. |
| 2008/0178879 A1 | 7/2008 | Roberts et al. |
| 2008/0190436 A1 | 8/2008 | Jaffe et al. |
| 2008/0196728 A1 | 8/2008 | Ho |
| 2008/0216838 A1 | 9/2008 | Wondka |
| 2008/0221470 A1* | 9/2008 | Sather .................. A61B 5/08 600/533 |
| 2008/0251079 A1 | 10/2008 | Richey |
| 2008/0276937 A1 | 11/2008 | Davidson et al. |
| 2008/0276941 A1 | 11/2008 | Doty et al. |
| 2009/0025723 A1 | 1/2009 | Schobel et al. |
| 2009/0044808 A1 | 2/2009 | Guney et al. |
| 2009/0056717 A1 | 3/2009 | Richards et al. |
| 2009/0065001 A1 | 3/2009 | Fishman |
| 2009/0071481 A1 | 3/2009 | Fishman |
| 2009/0101147 A1 | 4/2009 | Landis et al. |
| 2009/0133697 A1 | 5/2009 | Kwok et al. |
| 2009/0145441 A1 | 6/2009 | Doshi et al. |
| 2009/0188493 A1 | 7/2009 | Doshi et al. |
| 2009/0194109 A1 | 8/2009 | Doshi et al. |
| 2009/0197240 A1 | 8/2009 | Fishman et al. |
| 2009/0205650 A1 | 8/2009 | Tanaka et al. |
| 2009/0217929 A1 | 9/2009 | Kwok et al. |
| 2009/0241965 A1 | 10/2009 | Sather et al. |
| 2009/0248057 A1 | 10/2009 | Kotler |
| 2009/0250066 A1 | 10/2009 | Daly |
| 2009/0260625 A1 | 10/2009 | Wondka |
| 2009/0266365 A1 | 10/2009 | Oberle |
| 2009/0306529 A1 | 12/2009 | Curti et al. |
| 2009/0308398 A1 | 12/2009 | Ferdinand et al. |
| 2010/0000534 A1 | 1/2010 | Kooij et al. |
| 2010/0043801 A1 | 2/2010 | Halling et al. |
| 2010/0065053 A1 | 3/2010 | Haveri |
| 2010/0069770 A1 | 3/2010 | Girshin et al. |
| 2010/0069820 A1 | 3/2010 | Zotz |
| 2010/0070050 A1 | 3/2010 | Mathis et al. |
| 2010/0071693 A1 | 3/2010 | Allum et al. |
| 2010/0168511 A1 | 7/2010 | Muni et al. |
| 2010/0192957 A1 | 8/2010 | Hobson et al. |
| 2010/0212663 A1 | 8/2010 | Vedrine et al. |
| 2010/0229865 A1 | 9/2010 | Boussignac |
| 2010/0252042 A1 | 10/2010 | Kapust et al. |
| 2010/0326441 A1 | 12/2010 | Zucker et al. |
| 2010/0326447 A1 | 12/2010 | Loomas et al. |
| 2011/0005528 A1 | 1/2011 | Doshi et al. |
| 2011/0005530 A1 | 1/2011 | Doshi et al. |
| 2011/0009763 A1 | 1/2011 | Levitsky et al. |
| 2011/0011397 A1 | 1/2011 | Ziv et al. |
| 2011/0011400 A1 | 1/2011 | Gentner et al. |
| 2011/0017207 A1 | 1/2011 | Hendricksen et al. |
| 2011/0023891 A1 | 2/2011 | Blach et al. |
| 2011/0030685 A1 | 2/2011 | Wilkinson et al. |
| 2011/0040158 A1 | 2/2011 | Katz et al. |
| 2011/0041855 A1 | 2/2011 | Gunaratnam et al. |
| 2011/0067704 A1 | 3/2011 | Kooij et al. |
| 2011/0067708 A1 | 3/2011 | Doshi et al. |
| 2011/0073110 A1 | 3/2011 | Kenyon et al. |
| 2011/0073116 A1 | 3/2011 | Genger et al. |
| 2011/0094518 A1 | 4/2011 | Cipollone et al. |
| 2011/0100369 A1 | 5/2011 | Zhang et al. |
| 2011/0108041 A1 | 5/2011 | Sather et al. |
| 2011/0114098 A1 | 5/2011 | McAuley et al. |
| 2011/0125052 A1 | 5/2011 | Davenport et al. |
| 2011/0146674 A1 | 6/2011 | Roschak |
| 2011/0209709 A1 | 9/2011 | Davidson et al. |
| 2011/0245579 A1 | 10/2011 | Bruggeman et al. |
| 2011/0271962 A1 | 11/2011 | White et al. |
| 2011/0290256 A1 | 12/2011 | Sather et al. |
| 2012/0080037 A1 | 4/2012 | Guyuron et al. |
| 2012/0111332 A1 | 5/2012 | Gusky et al. |
| 2012/0118286 A1 | 5/2012 | Barodka |
| 2012/0125332 A1 | 5/2012 | Niland et al. |
| 2012/0157794 A1 | 6/2012 | Goodwin et al. |
| 2012/0167894 A1 | 7/2012 | O'Leary |
| 2012/0192869 A1 | 8/2012 | Hayek |
| 2012/0192870 A1 | 8/2012 | Dugan et al. |
| 2012/0209096 A1 | 8/2012 | Jaffe et al. |
| 2012/0247480 A1 | 10/2012 | Varga |
| 2012/0285463 A1 | 11/2012 | Dillingham et al. |
| 2012/0285470 A9 | 11/2012 | Sather et al. |
| 2012/0325205 A1 | 12/2012 | Allum et al. |
| 2012/0325206 A1 | 12/2012 | Allum et al. |
| 2012/0325218 A1 | 12/2012 | Brambilla et al. |
| 2013/0008447 A1 | 1/2013 | Gunaratnam et al. |
| 2013/0014754 A1 | 1/2013 | Guerra et al. |
| 2013/0019864 A1 | 1/2013 | Wondka |
| 2013/0092159 A1 | 4/2013 | Ulrichskotter et al. |
| 2013/0092165 A1 | 4/2013 | Wondka |
| 2013/0092173 A1 | 4/2013 | Alexander et al. |
| 2013/0104888 A1 | 5/2013 | Landis et al. |
| 2013/0104901 A1 | 5/2013 | Landis et al. |
| 2013/0158475 A1 | 6/2013 | Xia et al. |

(56) References Cited

U.S. PATENT DOCUMENTS

| | | |
|---|---|---|
| 2013/0184602 A1 | 7/2013 | Brambilla |
| 2013/0190643 A1 | 7/2013 | Brambilla |
| 2013/0211275 A1 | 8/2013 | Curti |
| 2013/0263854 A1 | 10/2013 | Taylor et al. |
| 2013/0312752 A2 | 11/2013 | Kapust et al. |
| 2013/0327334 A1 | 12/2013 | Pierro et al. |

OTHER PUBLICATIONS

PCT International Search Report and Written Opinion in PCT/US2013/073082, dated Apr. 3, 2014, 17 pages.
PCT International Search Report and Written Opinion in PCT/US2013/073142, dated Apr. 3, 2014, 17 pages.
Non-Final Office Action in U.S. Appl. No. 14/096,910, dated Apr. 25, 2014, 45 pages.
Final Office Action in U.S. Appl. No. 14/096,910, dated Dec. 19, 2014, 19 pages.
Non-Final Office Action in U.S. Appl. No. 14/312,003 dated May 11, 2016, 32 pages.
Extended European Search Report in Appln. No. EP 16204677.5 dated Feb. 28, 2017, 7 pages.

\* cited by examiner

DU 020.001 SD Seating suggestion

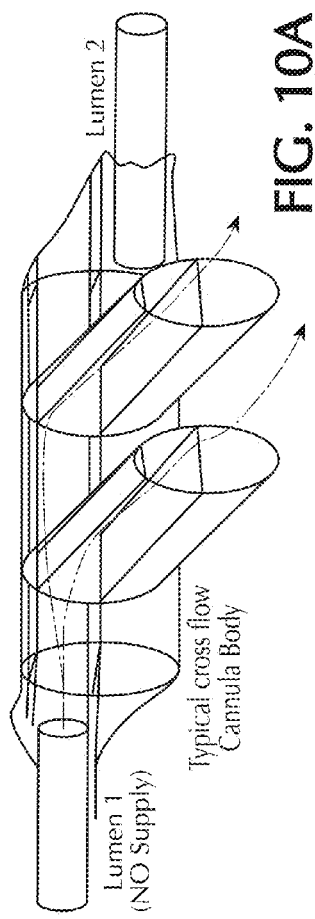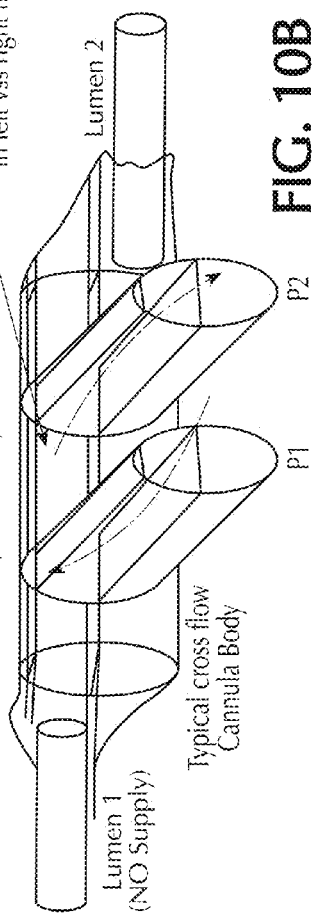

CANNULA FOR MINIMIZING DILUTION OF DOSING DURING NITRIC OXIDE DELIVERY

CROSS-REFERENCE TO RELATED APPLICATIONS

This application claims, under 35 USC §119(e), the benefit of U.S. Provisional Application No. 61/733,134, filed Dec. 4, 2012 and U.S. Provisional Application No. 61/784,238, filed Mar. 14, 2013 the contents of both of which are hereby incorporated by reference in their entireties.

TECHNICAL FIELD

Embodiments of the present invention generally relate to the field of methods and devices for nitric oxide delivery.

BACKGROUND

Nitric oxide (NO) is a gas that, when inhaled, acts to dilate blood vessels in the lungs, improving oxygenation of the blood and reducing pulmonary hypertension. Because of this, nitric oxide is provided as a therapeutic gas in the inspiratory breathing gases for patients with pulmonary hypertension.

Typically, inhaled NO is delivered in a carrier gas from a high pressure source (such as a pressurized cylinder) to the patient at or near ambient pressure by means of a respiratory tube for ICU ventilator bound or anesthesia patients or a nasal cannula for spontaneously breathing patients. It is particularly challenging to deliver an accurate and consistent dose to the patient through a nasal cannula as dilution of the dose can occur through retrograde flow and diffusion of other gases.

Delivery of NO may require transit through a nasal cannula. During patient inhalation and exhalation, a driving pressure gradient can cause retrograde flow in the nasal cannula supply lumen, thereby diluting the NO dose in the cannula with exhaled gas. In addition, diffusion of ambient gasses can occur through the cannula itself during the transit time of NO through the cannula. Oxygen is of specific concern as it reacts with NO to form nitrogen dioxide ($NO_2$) thereby reducing the NO concentration. This is further exacerbated by the fact that patients on NO may also require oxygen therapy. Both of these issues can dilute the delivered dose of NO during inhaled NO therapy.

Accordingly, there is a need for new methods and apparatuses for preventing dilution of dosing within the delivery conduit of a nitric oxide delivery apparatus.

SUMMARY

Aspects of the present invention relate to improved nasal cannulas that minimize retrograde flow and permeation of oxygen during NO therapy while allowing NO delivery to both nares of the nostril. Such cannulas may reduce dilution of the delivered dose by using cannula materials that limit oxygen diffusion through the cannula walls and/or utilize cannula configurations that prevent mixing of co-delivered $O_2$ and NO and/or reduce retrograde diffusion through the patient end of the cannula. Aspects of the present invention also relate to methods of minimizing the dilution of the NO dose. Other aspects pertain to methods of treatment utilizing these nasal cannulas and/or methods of administration.

Other aspects of the invention relate to methods of manufacturing multi-lumen cannulas and their nosepieces.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawing. It is to be noted, however, that the appended drawing illustrates only typical embodiments of this invention and are therefore not to be considered limiting of its scope, for the invention may admit to other equally effective embodiments.

FIGS. 10A and 10B show cross-flow between two nasal cannula prongs;

DETAILED DESCRIPTION

Figure 1:
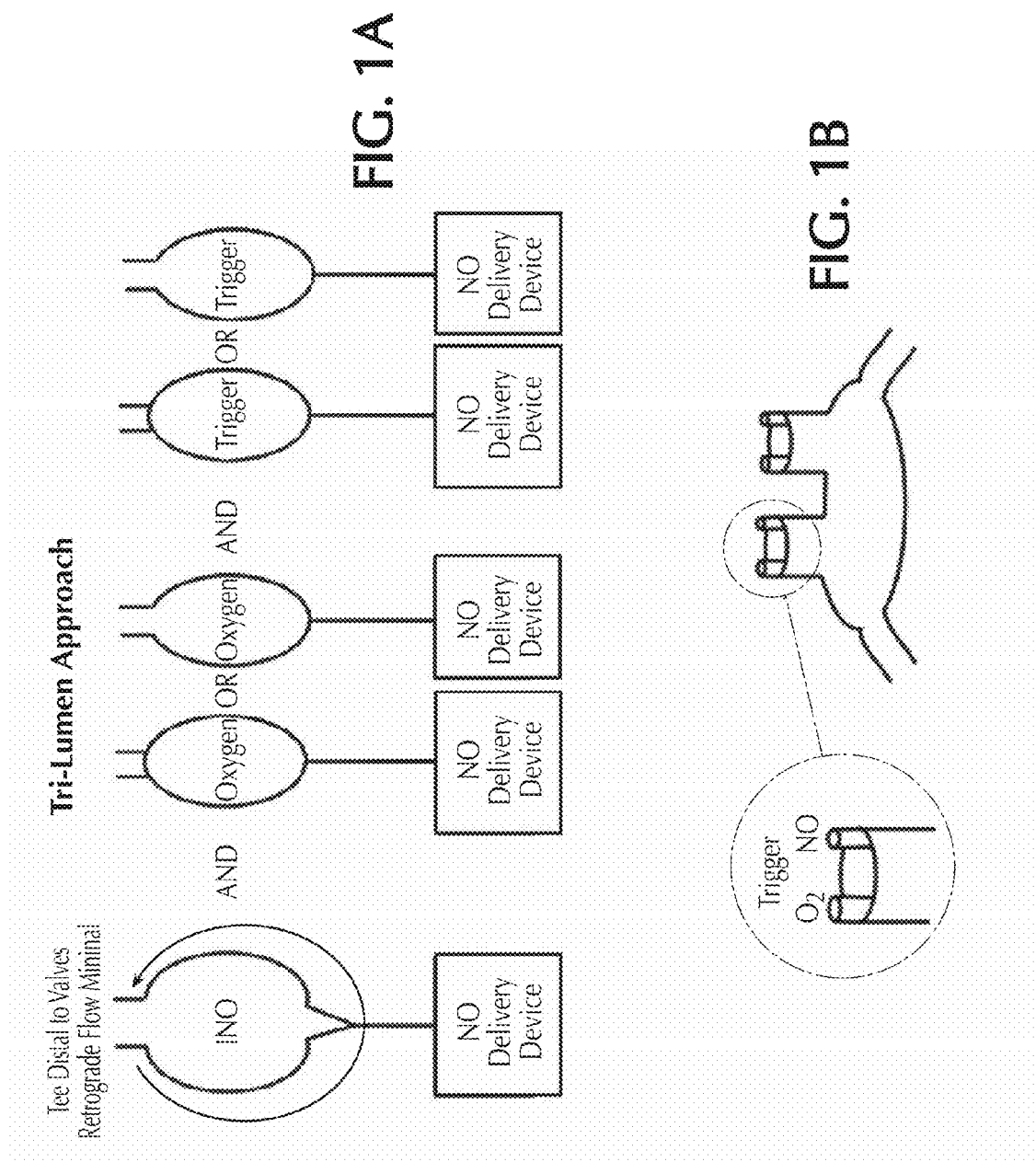
FIGS. 1A and 1B show the pneumatic paths for the NO, oxygen and trigger lines in a tri-lumen cannula.

Methods of delivering inhaled nitric oxide (NO) should ideally be optimized to ensure accurate and consistent delivery of the dose to the patient. Typically, NO is delivered at relatively low volumetric percent concentrations in a carrier gas. Nitrogen is a common carrier gas for NO delivery because nitrogen is non-reactive with NO, but other inert carrier gases such as helium may be used. Delivery of the $NO/N_2$ gas mixture to the patient typically requires that the gas travel from a high pressure NO source (such as a pressurized cylinder) to the patient at or near ambient pressure by means of a respiratory tube for ICU ventilator bound or anesthesia patients or a nasal cannula for spontaneously breathing patients. This travel of the NO is ideally devoid of contact with other gasses, such as ambient air, oxygen, carbon dioxide, etc., until the gas enters the patient's upper respiratory tract. However, in practice, this is not easily achieved. Specifically, oxygen and ambient air can enter the delivery system at a number of points as follows:

During the connection of the high pressure source (typically cylinder) to the delivery device During the NO gas transit through the cannula (by way of diffusion across the cannula wall)

During the inhalation/exhalation cycle when a driving pressure gradient seeks to reverse flow in the nasal cannula NO supply lumen producing mixing within the cannula with ambient air The dilution of NO during pulsed NO therapy may be problematic because only a small volume of NO is delivered to the patient. For example, the NO-containing gas may be administered in pulses less than 1 mL. With small pulse volumes, even small volumes of retrograde flow or diffused gases may be significant because the NO dose may be diluted.

Materials:

One or more embodiments of the present invention relate to a nasal cannula that addresses one or more of these above sources of oxygen/NO contact and thereby dilution of the intended NO dose. One particular source of oxygen that may be minimized is the transit of oxygen across the cannula walls. In one or more embodiments, a cannula is provided that includes a smaller inside diameter (ID) delivery tube/lumen for NO. This smaller ID tube reduces the transit time of the NO molecules through the cannula, thereby reducing the time available for oxygen to diffuse across the walls of the cannula and oxidize the internal NO into $NO_2$.

Another approach to minimize the oxygen contact provided by oxygen diffusion across the cannula walls is to use a wall material that minimizes the oxygen diffusion rate. Accordingly, in some embodiments, the cannula wall comprises a material with a low oxygen diffusion coefficient. Polyvinyl chloride (PVC) is currently a common material for constructing nasal cannulas, but it is not optimal for reducing oxygen diffusion through the cannula walls. Accordingly, some embodiments provide using urethane or another similar soft material. In some embodiments, the urethane or other soft material includes an additive to enhance the resistance to oxygen diffusion. Examples of suitable additives include oxygen resistant polymers such as polyvinylidene chloride (PVDC), ethylene vinyl alcohol (EVOH), polyamide (PA) or similar materials. Alternatively, PVC may be used as the cannula material, but one or more additives such as oxygen resistant polymers may be incorporated to reduce the oxygen diffusion coefficient of the material. The oxygen resistant polymers may be incorporated into the urethane or other cannula material through co-extrusion. Such an extrusion may be achieved with a dual head extruder.

Pneumatic Configurations:

Another potential source of nitric oxide dilution is from retrograde flow in the nasal cannula. Retrograde flow, also known as cross flow, is a phenomenon in which ambient air flows in opposite directions between the two delivery prongs of the nasal cannula. As shown in FIG. 10A, during normal pulsed delivery, NO flows out of both nasal prongs of the cannula. However, during the static phase between pulses, ambient air can flow in a circular motion in through one prong and out the other prong as shown in FIG. 10B. The degree of retrograde flow depends on the pressure difference between the nares during both the inhalation and exhalation phase. The pressure difference between the nares can vary depending on the person's breathing pattern, placement of the nasal prongs and the degree of misbalance between the nasal flow during breathing. Retrograde flow results in dilution and washout of the NO in the nasal prongs and flow path. This can cause a delay or reduction in the delivered dose. Furthermore, air may react with nitric oxide in the nasal cannula, thus forming $NO_2$ and further diluting the NO concentration.

Accordingly, aspects of the present invention also provide nasal cannulas that may minimize the retrograde flow in the nasal cannula. Such nasal cannulas may include a means of delivering oxygen and therapeutic gas containing NO, and may be able to transmit pressure transients associated with inhalation-based gas flow triggering. If the cannulas deliver oxygen in addition to NO, the oxygen may be provided by an oxygen conserver or an oxygen concentrator.

Figure 11:
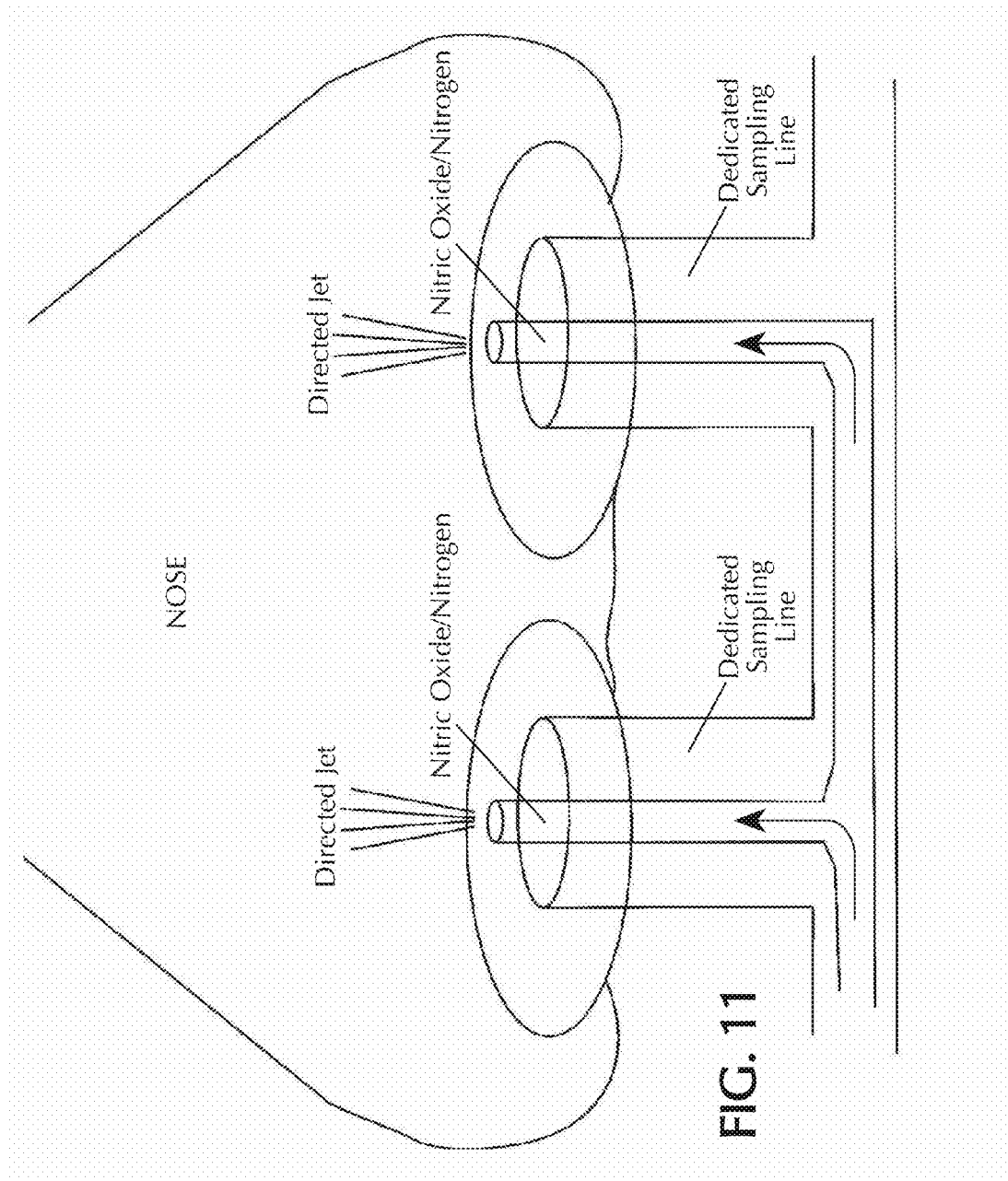
FIG. 11 shows a nasal cannula with two lumina of different sizes.

In one or more embodiments, the nasal cannula has two lumina (i.e. a dual-lumen cannula). FIG. 11 shows an exemplary dual-lumen cannula that delivers nitric oxide in a separate lumen than is used to deliver oxygen and/or trigger the delivery device. The NO lumen carries therapeutic gas comprising NO from the NO delivery device to the patient. The trigger lumen does not deliver gas to the patient, but instead establishes fluid communication between the patient's nares and a trigger sensor in the NO delivery device. When the patient begins a breath, a drop in pressure occurs in the nares. This pressure signal is communicated through the trigger lumen to the trigger sensor, which then senses that the patient has begun inspiration. The trigger sensor can then send a signal to a CPU in the NO delivery device so that the CPU will open a control valve to deliver NO to the patient, such as a pulse of NO in a carrier gas.

As shown in FIG. 11, in some embodiments the lumen that carries the nitric-oxide containing gas may have a smaller inner diameter than the other lumen such as the triggering lumen. In these embodiments, the cannula may reduce dilution by at least two potential mechanisms: 1) the cannula may minimize mixing of oxygen and NO by two means, first a reduction in retrograde flow into the small ID NO carrying lumen due to the smaller, ID, second the volume of gas per unit length is reduced thereby reducing the bulk volume of gas mixing occurring; and 2) the narrow ID produces a narrow jet of gas flow which effectively minimizes $O_2$/NO mixing during NO delivery until much further into the nasal cavity. The diameter of the small lumen may be minimized by engineering design such that it is as small as reasonably possible without producing confounding upstream effects on the flow delivery mechanics of the device. In some embodiments, the ratio of the ID of the NO lumen to the ID of the trigger lumen may be 1:1, 1:1.2, 1:1.3, 1:1.5, 1:2, 1:2.5, 1:3, 1:3.5, 1:4, 1:4.5, 1:5, 1:5.5, 1:6, 1:7, 1:8, 1:9, 1:10, 1:12, 1:15, 1:20, 1:25 or 1:30.

Also, the geometry of the nasal cannula lumina may be optimized to prevent retrograde flow. Thus, in addition to circular or parabolic cross-sections, the cross-section of any of the nasal cannula lumina described herein may be square, rectangular, triangular or any other regular or irregular shape to minimize dose dilution. When one or more cross-sectional areas are not circular, then the ratio of inner diameters may be the square root of the ratio of the surface areas of the two lumina sections.

Figure 13:
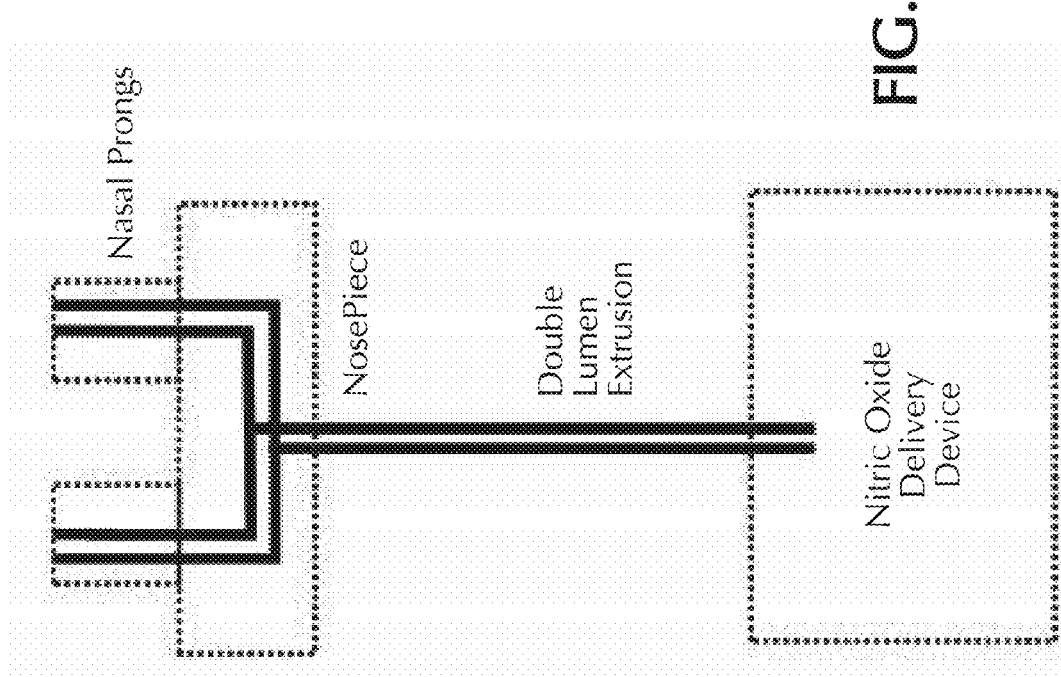
FIG. 13 shows a dual-lumen cannula for co-delivering NO and $O_2$.

Alternatively, a dual-lumen cannula may have a first lumen for oxygen delivery and a second lumen for delivery of NO and transmitting the pressure signal for the trigger sensor. Such a two lumina configuration is shown in FIG. 13.

In this configuration, the first lumen carries oxygen from the oxygen conserver/concentrator to the nosepiece of the cannula. The second lumen delivers NO from the nitric oxide delivery device to the patient and delivers the pressure-based triggering signal from the patient to trigger sensor of the nitric oxide delivery device. Both lumina would be constructed to "tee" to both nares and thus be in unobstructed fluid communication with both nares as shown in FIG. 13.

The first lumen for carrying oxygen may be constructed with lumen inner diameter geometry consistent with industry norms. For instance, nasal cannulas with rated 6 LPM oxygen delivery capacity typically provide an oxygen lumen inner diameter of approximately 0.080" at or near the nosepiece.

The second lumen of the dual-lumen cannula may have a geometry unique to the gas delivery objectives of the nitric oxide delivery system. Nitric oxide delivery systems which pulse nitric oxide gas into the patient are believed to have optimal clinical efficacy when a pulse or flow of nitric oxide is delivered to the patient as early in the inspiratory phase as possible. Therefore, any pneumatic delays would not be optimal. Further, the shape of the flow waveform as delivered by the nitric oxide delivery system is, optimally, not distorted during transit from the device to the patient. In addition, the transit of the pressure signal from the patient indicative of inspiratory effort preferably is not delayed/distorted when in transit from the patient back to the device. Finally, the volume of potential nitric oxide mixing with either exhaled gas or ambient gas is preferably minimized to reduce the potential for oxidation of nitric oxide at the nosepiece of the cannula, which again can produce $NO_2$ which dilutes the NO dose and is a known respiratory irritant.

In order to achieve the goals described above for the second lumen, there are several competing metrics of lumen ID optimization as noted below:
  a. Reduce $NO_2$ formation→Reduce lumen ID
  b. Maintain volumetric NO dosing accuracy→Reduce lumen ID
  c. Reduce NO flow distortion→Lumen ID within certain bounds
  d. Minimize trigger signal attenuation or delay→Increase lumen ID Therefore, an optimal inner diameter dimension of the second lumen would address all of these concerns to ensure adequate device performance. Such optimal ID dimensions may vary depending on the volume of NO-containing gas delivered by the nitric oxide delivery device. For example, a nitric oxide delivery device may deliver pulses of NO-containing gas with a minimum dose volume of 0.35 mL. In order to ensure volumetric dosing accuracy, it is preferable that no more than 10% of the dose can be lost due to ambient bleed of NO in between inspiratory efforts. Such a bleed can occur during the exhalation phase in which imbalances in the flow out of the nostrils results in a "high flow nostril" and a "low flow nostril." Flow into the prong from the high flow nostril may result in flow of out of (gas loss out of) the prong of the low flow nostril. This gas, which is located in the "U" shaped portion of the tee'd lumen, is lost to ambient during the exhalation phase and would consist of NO therapeutic gas. Therefore, one or more embodiments of the present invention limit the internal volume of this "U" shape to be no more than 10% of the minimum dose volume (i.e. 0.035 mL for a 0.35 mL pulse of therapeutic gas), thus ensuring acceptable NO loss to ambient during the exhalation phase. Such a requirement of 0.035 mL requires a lumen ID within the "U" segment of no more than 0.046" given a prong length of 8 mm and a prong spacing of 16 mm. Therefore, a lumen ID significantly larger than 0.046" would not be advantageous to maintaining dose volume accuracy for minimum dose volumes of 0.35 mL. Of course, it is understood that the mathematics of this construct would be modified by systems with larger or smaller minimum dose volumes appropriately, or with different prong lengths and/or prong spacing. One skilled in the art can perform the required calculations to determine the ID required to provide a desired volume in the "U" section so that it does not exceed 10% of the dose volume. Furthermore, depending on the required accuracy for the dosing, the internal "U" volume or other volume available for cross-flow may be less than 50%, 45%, 40%, 35%, 30%, 25%, 20%, 15%, 10%, 5%, 4%, 3%, 2% or 1% of the dose volume.

In addition to the volumetric dosing accuracy concern, another concern is that the second lumen ID not produce gas flow distortion. However, given that gas flow in a nitric oxide system may use restrictors which are significantly smaller in inner diameter than a NO lumen ID of 0.046 inches, such distortion may not actually occur.

Finally, the inner diameter of the second lumen preferably does not produce undue signal propagation delay from the patient to the device. Such delay is believed to occur as pneumatic tubes behave as first order pneumatic low pass filters and attenuate higher bandwidth signal components. Modification of the inner diameters is known to change the band pass characteristics of the filtering effect. However, as noted earlier, the inner diameter (at the U) may be fixed to a certain maximum ID based on the required dose delivery accuracy of the system. Therefore, in order to minimize the effects of the potentially frequency attenuated pressure signal, two measures can be taken. First the upstream (close to device) diameter of the second lumen may be adjusted to widen (optimize) the band pass characteristics of the cannula. This may ensure that unneeded compressible volume is unavailable upstream of the nose piece restriction (0.046" ID restriction). This reduces the compressible volume in the cannula and effectively increases the bandpass characteristics of the cannula. The second measure which can be taken is to trigger the initiation of pulse delivery on the device not based on a threshold pressure level (the magnitude of which can which can be delayed by frequency attenuation) but by triggering the device based on a pattern of sloping pressure indicative of patient effort. Such a slope may be reduced in magnitude by the filtering characteristics of the tubing, however, the slope will still be present for algorithmic triggering decisions by the device. However, such a triggering implementation is optional.

Accordingly, in some embodiments, the dual lumen cannula would have an oxygen lumen in the range from 0.05 to 0.12" ID (such as about 0.080" ID) which tees at the nosepiece and is in fluid communication with both nares. It would also have a second (nitric oxide) lumen (similarly in fluid communication with both nares) with an internal tubing diameter dictated by volumetric dosing accuracy considerations and the second lumen may have an ID in the range from 0.01 to 0.08" (such as about 0.046" ID) with upstream tubing adjusted to optimize the bandpass performance of the system. Finally, device triggering methodologies based not on pressure thresholds, but based on pressure slope trends can also be employed to improve overall timely delivery of dosing to the patient.

Other pneumatic configurations for the nasal cannula may utilize different numbers of lumina. In one or more embodiments, the nasal cannula has three lumina (i.e. a tri-lumen cannula). FIG. 1A shows an exemplary set of pneumatic paths of the three individual lumen from a nitric oxide delivery device to the patient. The three lumina may include a NO lumen, a trigger sensor lumen and an oxygen lumen. The oxygen lumen carries an oxygen-enriched gas (such as oxygen-enriched air or substantially pure oxygen) from an oxygen source to the patient. The oxygen source may be a typical oxygen pulsing device, or may be a port on the NO delivery device that delivers the oxygen-enriched gas. FIG. 1B shows the three lumina aggregated into a single cannula. In FIGS. 1A and 1B, the NO lumen is tee'd at some point between the patient and the NO delivery device. Further, the oxygen and trigger lumina are also tee'd at some point between the device and the patient and might be tee'd in two locations, such as having an additional tee in the cannula head at the two nasal prongs.

Figure 2:
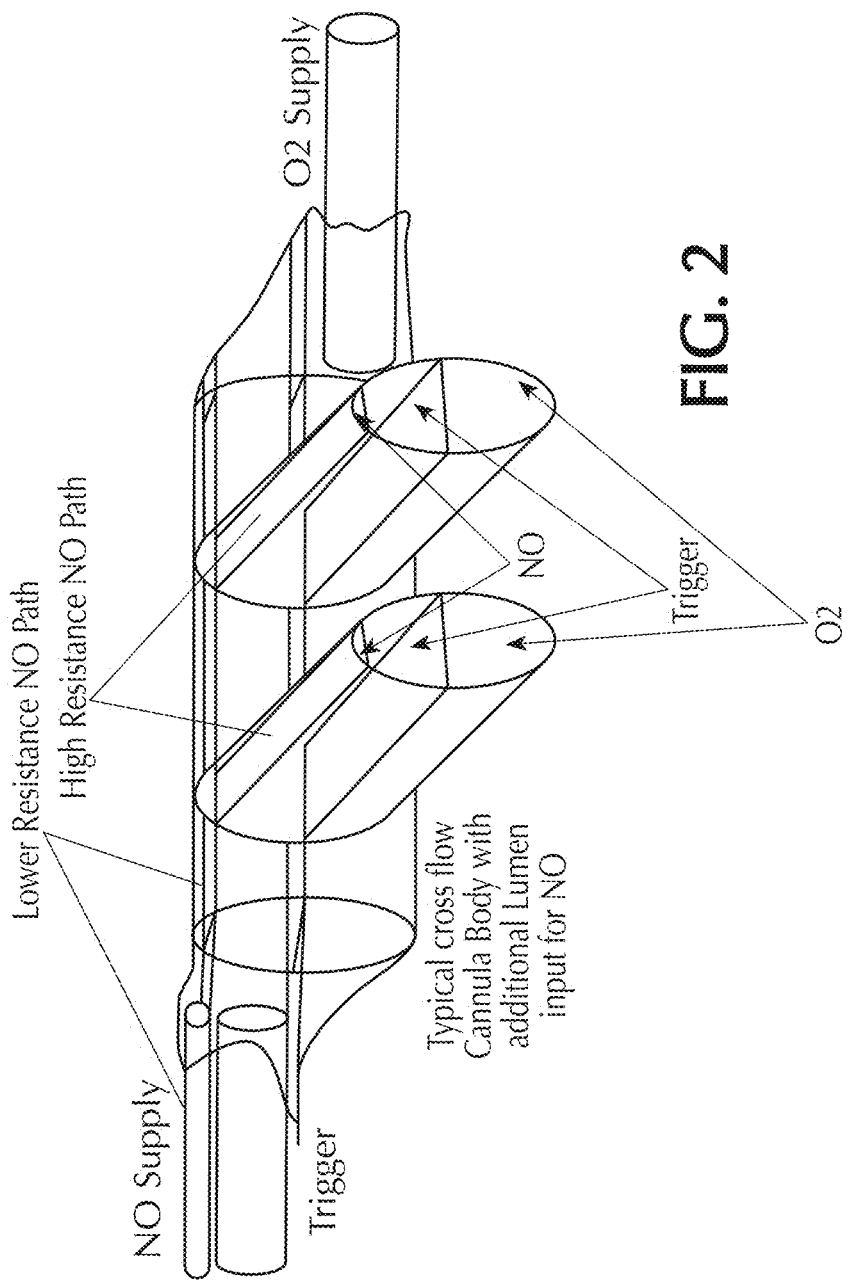
FIG. 2 shows three lumina integrated into a single cannula head.

Again, all three of the lumina may be integrated into a single cannula. FIG. 2 shows one such method for integration of the three lumina at the head (nose bridge fitting) of the cannula. The separation of the pneumatic paths or lumina in FIG. 2 is by means of partitions or diaphragms within the head and prongs of the cannula. The NO supply traverses to the head through a lower gas resistance source to higher resistance orifices integrated into the prongs of the cannula. All lumina are separated by a diaphragm partition within the head of the cannula and within the prongs of the cannula, which prevents mixing of the fluid streams in the separate lumina.

Figure 3:
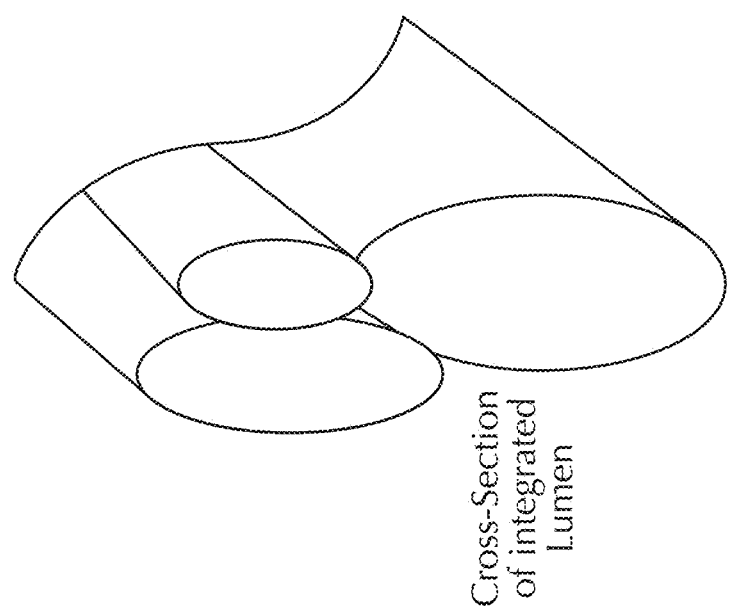
FIG. 3 shows a cross-section of an integrated three-lumina cannula.

The tubes of the cannula carry backwards towards the patient and may be affixed to each other so as to produce a clean single element umbilical between the cannula head and the device as shown in FIG. 3, which provides a cross-section. Alternately, the three lumina can be extruded through a single die producing a multi-lumen tube.

As can be seen from FIG. 2, the NO delivery tube may decrease in inner diameter (ID) once the tubing enters the head of the nasal cannula. Accordingly, in one or more embodiments, the pneumatic resistance is greater in the prongs of the nasal cannula than in the tubing carrying the NO from the NO delivery device to the cannula head. Such a device may have many advantages. In some embodiments, the smaller ID tubing of the dedicated NO delivery lumen will allow for:

Short gas transit times

Reduced inspiratory/expiratory phase retrograde flow of ambient air into the lumen (reduced according to Knudsen diffusion which states that diffusion rate is proportionate to the mean free path length of the gas molecule which is reduced with smaller ID)

Increased gas resistance to flow (smaller ID tubing produces gas flow resistance which is inversely proportional to the fourth power of tubing radius by Poiseuille's Law).

Reduced volume in the tee'd loop of the NO delivery lumen

All of the above may serve to reduce the potential for retrograde flow and/or reduce the volume of retrograde flow and/or reduce the contact or contact duration between NO and other gasses including oxygen in the cannula. This will reduce the dilution of NO and thereby increase the precision of the delivered NO dose.

The ID of the NO lumen may decrease from a maximum ID to a minimum ID. In some embodiments, the ratio of the minimum ID to the maximum ID of the NO lumen may be 1:1, 1:1.2, 1:1.3, 1:1.5, 1:2, 1:2.5, 1:3, 1:3.5, 1:4, 1:4.5, 1:5, 1:5.5, 1:6, 1:7, 1:8, 1:9 or 1:10.

The trigger lumen ID may be comparatively much larger than the NO lumen ID. Trigger pressure drop on inhalation must be transmitted through this cannula lumen with the smallest possible loss of signal magnitude to the NO delivery device which in turn uses this pressure signal to deliver pulsed NO. Again, in some embodiments, the ratio of the ID of the NO lumen to the ID of trigger lumen may be 1:1, 1:1.2, 1:1.3, 1:1.5, 1:2, 1:2.5, 1:3, 1:3.5, 1:4, 1:4.5, 1:5, 1:5.5, 1:6, 1:7, 1:8, 1:9, 1:10, 1:12, 1:15, 1:20, 1:25 or 1:30.

The oxygen lumen may also be larger than the NO lumen to minimize oxygen flow resistance and to reduce gas flow speed at the prongs which could serve to interfere with the triggering pressure signal due to gas flow effects such from Bernoulli's principle. As with the trigger lumen, in some embodiments the ratio of the ID of the NO lumen to the ID of the oxygen lumen may be 1:1, 1:1.2, 1:1.3, 1:1.5, 1:2, 1:2.5, 1:3, 1:3.5, 1:4, 1:4.5, 1:5, 1:5.5, 1:6, 1:7, 1:8, 1:9, 1:10, 1:12, 1:15, 1:20, 1:25 or 1:30.

Figure 4A:
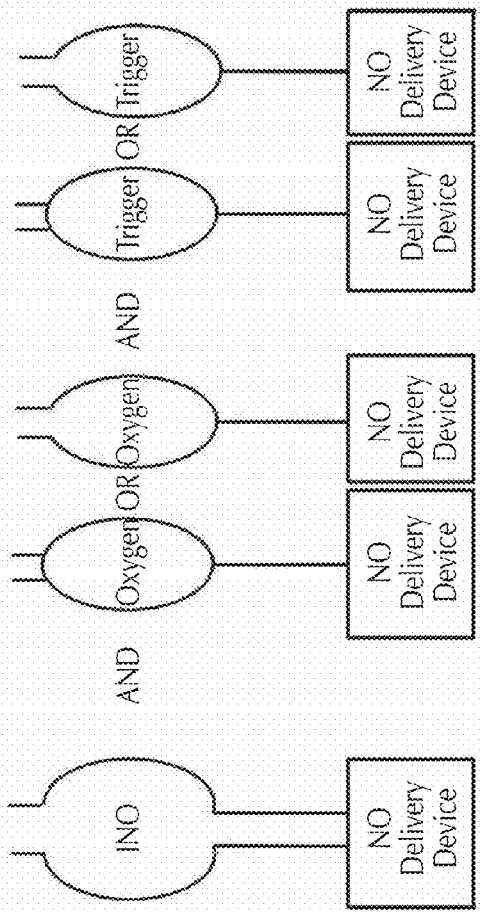
FIGS. 4A and 4B show the pneumatic paths for the NO, oxygen and trigger lines in a quad-lumen cannula.
Figure 4B:
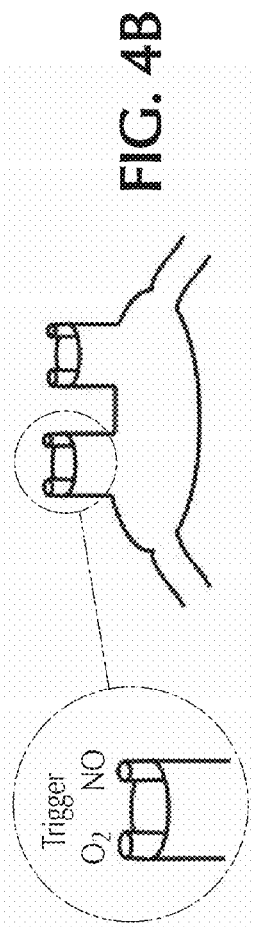

Another pneumatic configuration is shown in FIGS. 4A and 4B. Like the pneumatic configurations shown in FIGS. 1A and 1B, this configuration separates the pneumatic paths of the NO, oxygen and trigger. However, unlike the configuration shown in FIGS. 1A and 1B, in the configuration shown in FIGS. 4A and 4B, the NO flow delivery paths to each nostril are kept separate and distinct and have their own pneumatic delivery source at the NO delivery device. Accordingly, this configuration has four lumina (i.e. a quad-lumen cannula).

One potential benefit of the quad-lumen approach is to prevent movement of gas through the tee'd delivery loop of the NO supply line during exhalation. This may reduce NO/oxygen contact. However, unlike the tri-lumen cannula, use of the quad-lumen cannula may require dedicated pneumatic circuitry for each NO lumen.

Figure 5:
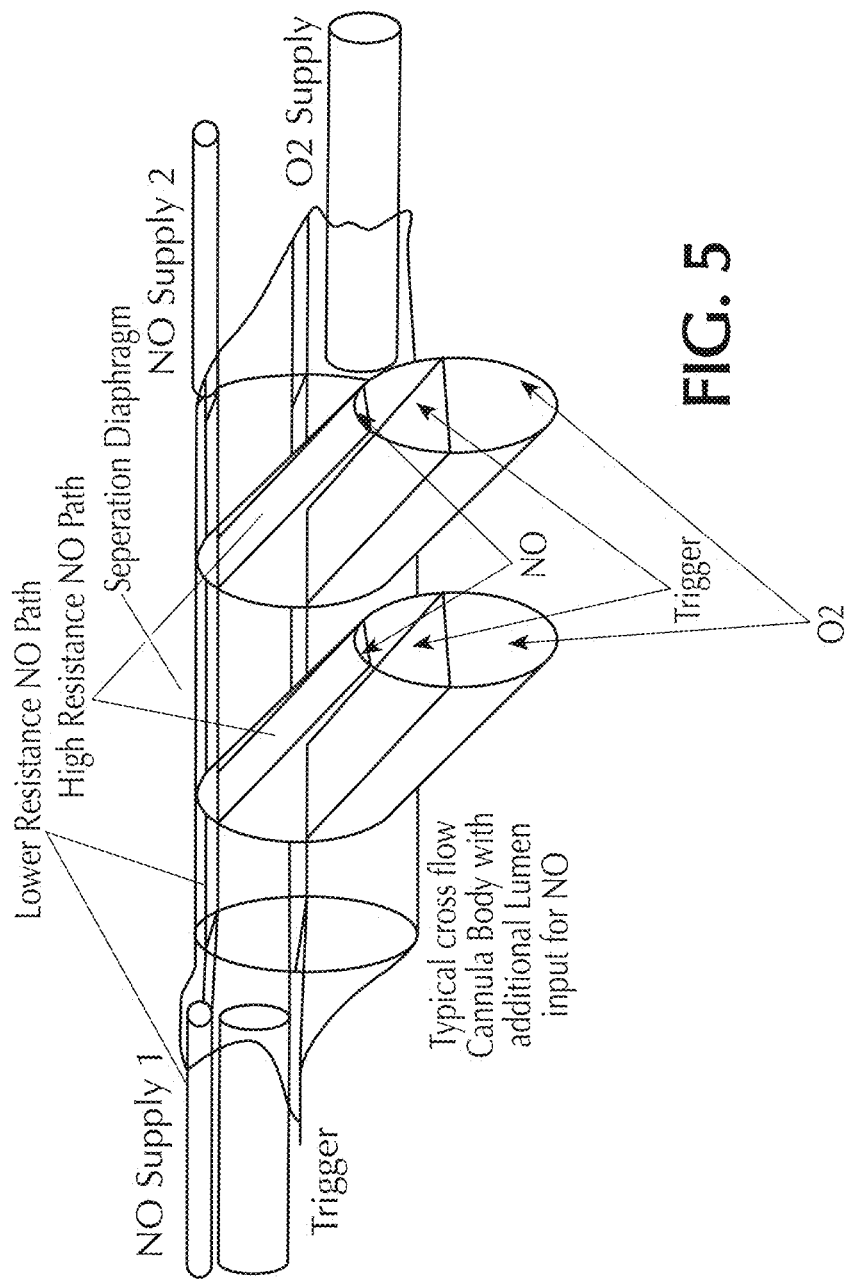
FIG. 5 shows four lumina integrated into a single cannula head.

FIG. 5 shows one potential method for achieving this configuration at the cannula head. As with the tri-lumen cannula, the quad-lumen cannula fuses the lumen of the cannula into a single umbilical between the cannula head and the device.

Figure 6B:
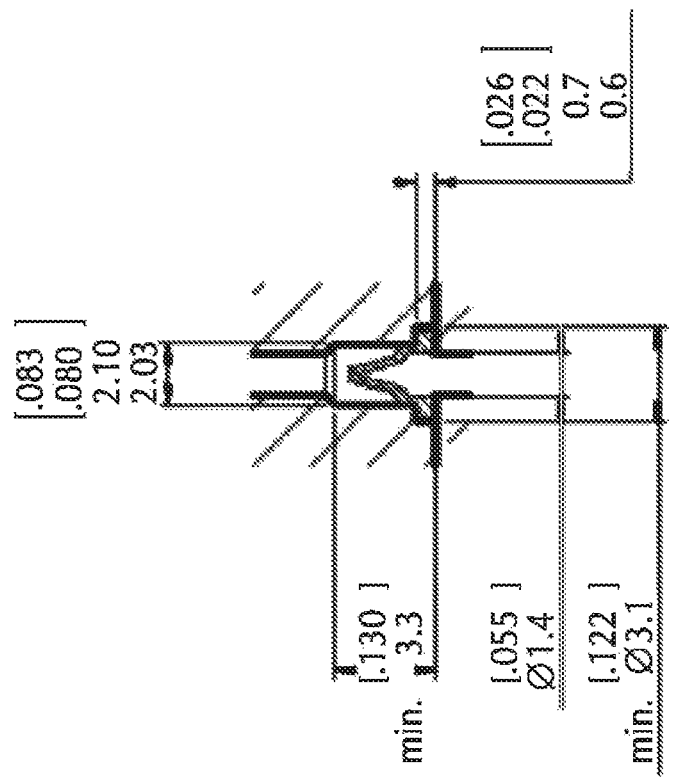
FIGS. 6A and 6B show details of duck bill check valves.
Figure 6A:
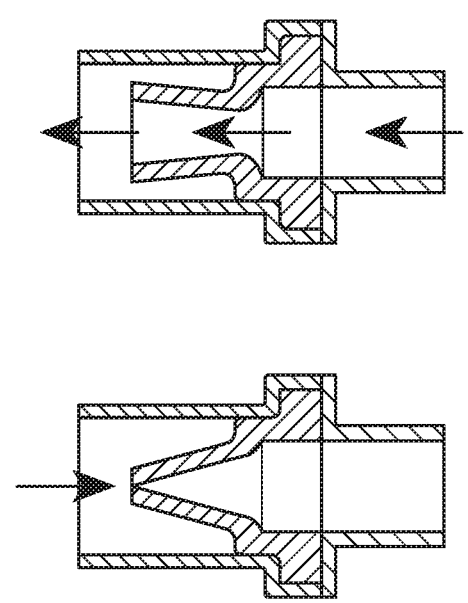
Figure 6D:
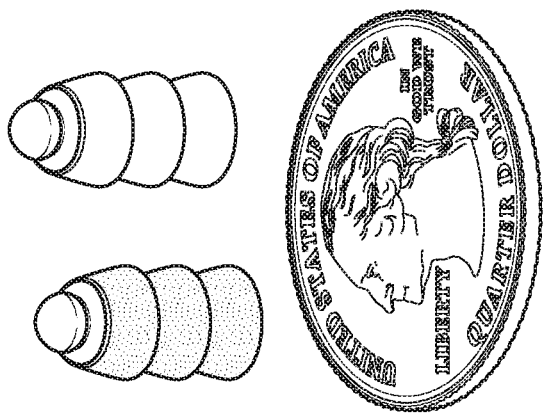
FIGS. 6C and 6D show details of umbrella check valves.
Figure 6C:
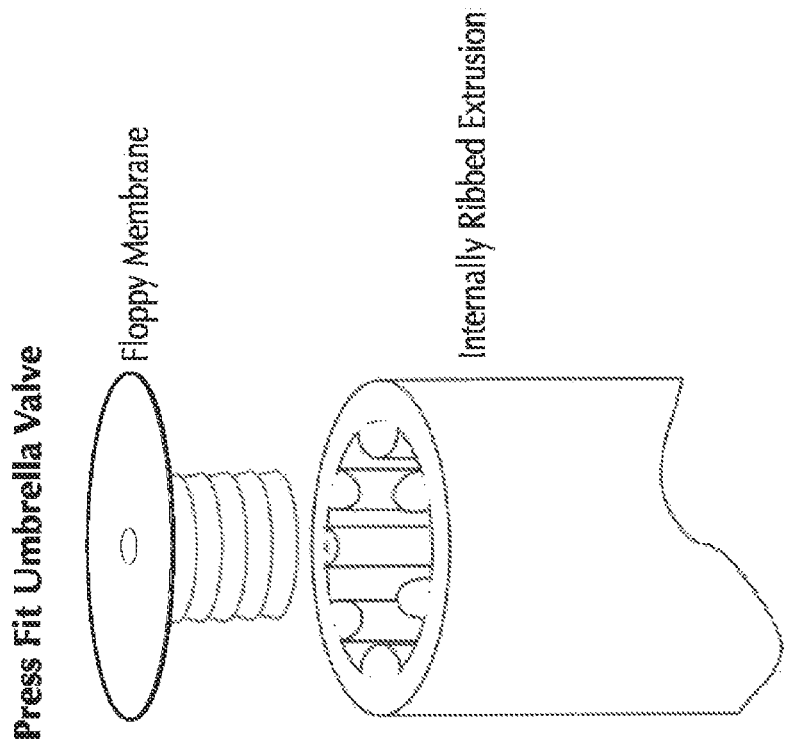

With any of the pneumatic configurations described herein, there may be other modifications of the cannula to improve NO dosing. In one or more embodiments, provided is a nasal cannula with one or more check valves in the nitric oxide delivery line. This configuration may be combined with one of the multi-lumen configurations described above. The check valves(s) help to prevent retrograde gas movement into the NO supply lumen during inhalation/exhalation. Such a check valve might consist of any low cracking pressure check valve which is placed at some point in the NO delivery path. Such check valves may include, but are not limited to, duckbill valves or umbrella valves. Exemplary duck bill valves are shown in FIGS. 6A and 6B and exemplary umbrella valves are shown in FIGS. 6C and 6D. These check valves may be miniature check valves so to have the proper dimensions to fit in the NO delivery lumen.

Figure 7:
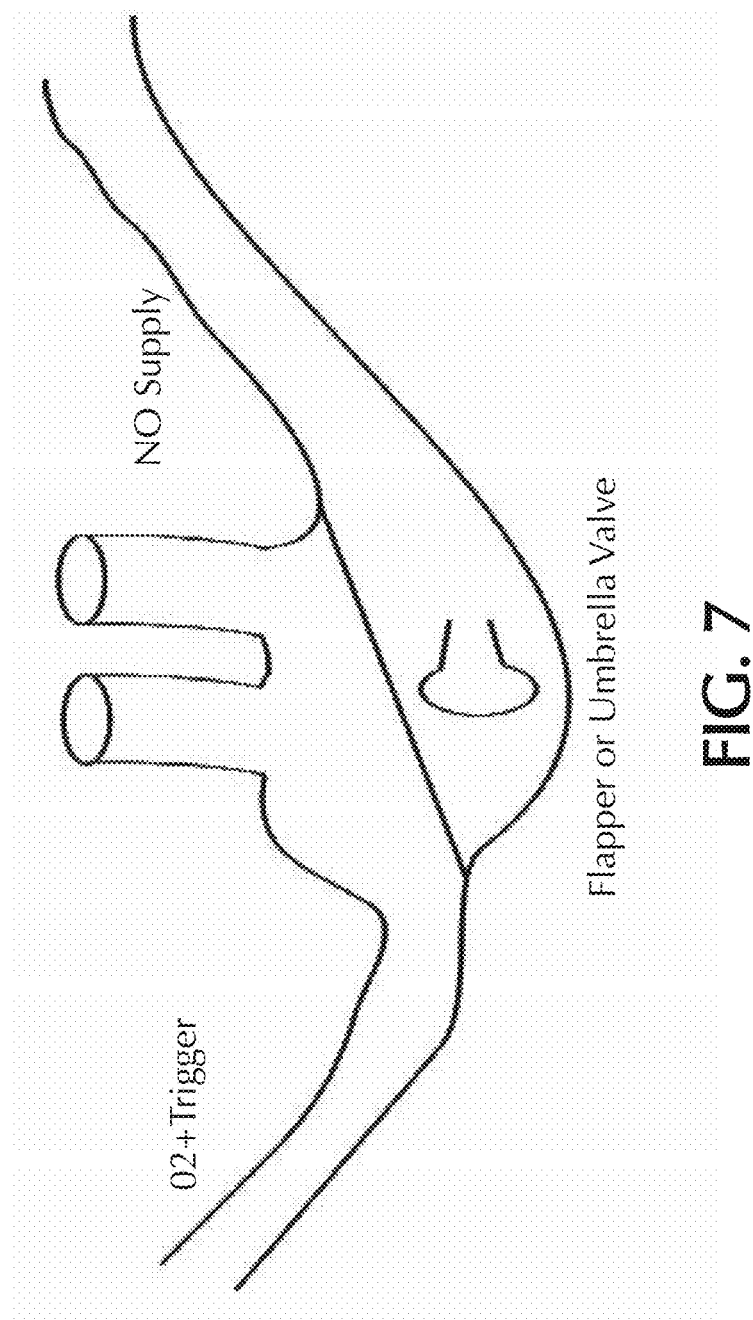
FIG. 7 shows a nasal cannula with an umbrella or flapper valve for delivering NO.

In one or more embodiments, provided is an NO delivery cannula having a small flapper or umbrella check valve at the head of the cannula allowing pulses of NO to be delivered to the general nose/mouth area during device NO pulsing. An exemplary configuration of a nasal cannula with such a flapper or umbrella valve is shown in FIG. 7. This configuration would allow NO to flow into either/both open nares upon inhalation. The $O_2$ and trigger lumen may be combined (as shown in FIG. 7) or kept separate to improve the signal-to-noise performance of the trigger lumen. Such a configuration with the flapper valve would prevent retrograde flow of oxygen into the NO delivery path thereby reducing the potential for dilution of the dose. A diaphragm or other barrier separates the NO delivery line from the O₂/trigger line at the cannula head to prevent mixing.

This pneumatic configuration may be combined with any of the other pneumatic configurations described above.

In one or more embodiments, also provided is a nasal cannula incorporating an impermeable or semi-permeable membrane. The membrane may be movable or fixed but can be actively or passively moved when needed, that separates the NO containing gas or material from the O₂ containing gas or material until the NO needs to be delivered to the patient. This membrane may reduce one or more of the contact time, surface area and diffusion rate between the NO and O₂ containing gases. This may reduce the formation of NO₂, which dilutes the intended NO delivery concentration.

Figure 12:
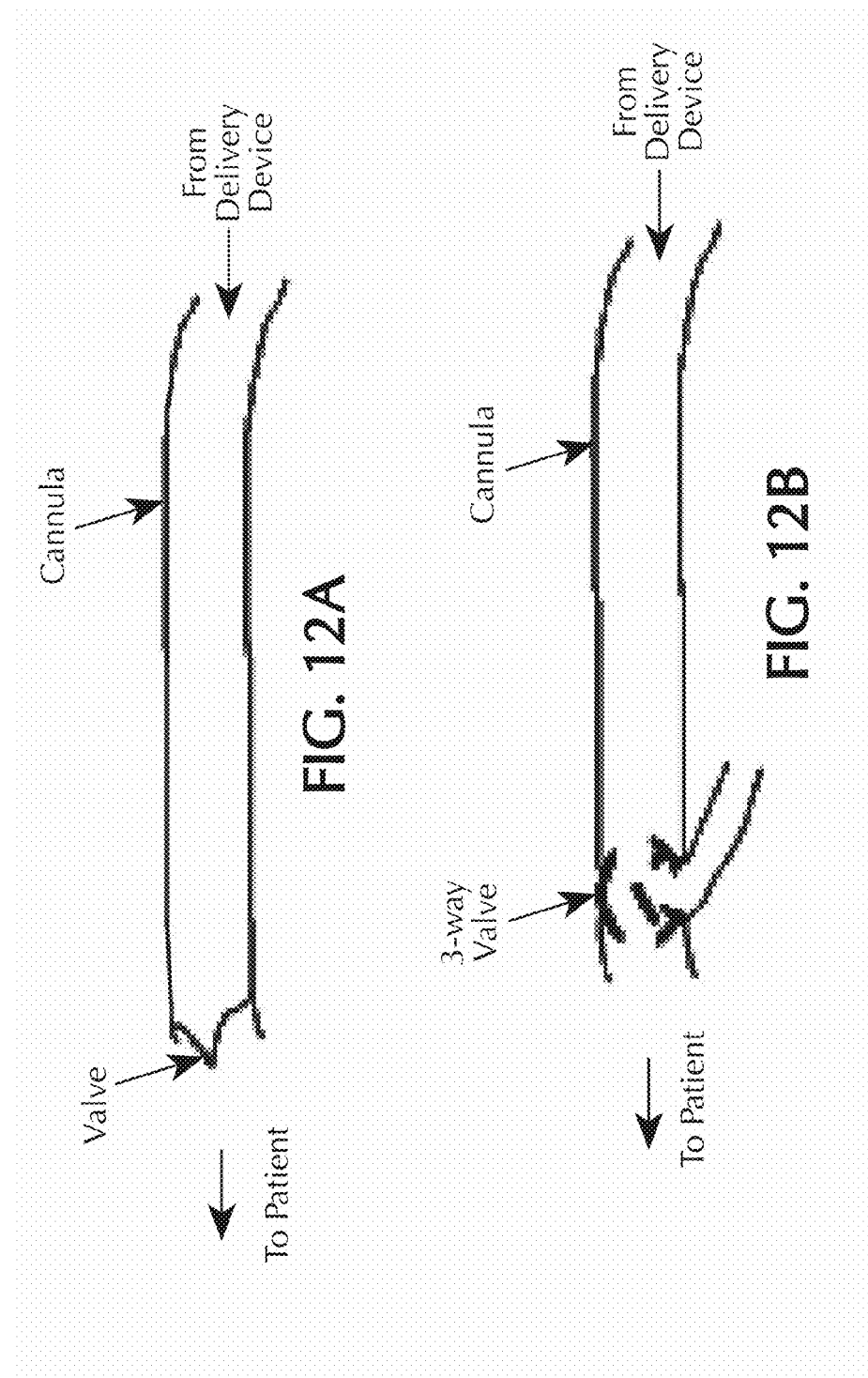
FIGS. 12A and 12B show two embodiments of incorporating a valve into the NO delivery line.

In some embodiments of the membrane, a normally-closed valve at the tip of the NO containing cannula prevents air from contacting the NO containing gas inside the cannula until the valve opening is triggered (e.g. by a drop in pressure caused by inhalation by the patient or by the positive pressure caused by the delivery device as it attempts to deliver the NO containing gas to the patient). When the valve opening is triggered, the NO is then delivered to the patient. One embodiment of such a valve is shown in FIG. 12A.

In one or more embodiments, also provided is a system to expel the gas or other NO containing material that does come in contact with O₂ containing gas or material, which may have otherwise formed NO₂ in this mixture. The system may subsequently allow another part of the NO containing gas or material that has minimal or no NO₂ to be delivered to the patient Again, this NO₂ formation could serve to dilute the NO dose before delivery to the patient.

In some embodiments of this system, this system may comprise an electromechanical valve system that actuates to pump out a fixed or adjustable amount of gas mixture that might contain NO₂ through a separate orifice than the cannula opening to the patient. The system may then actuate to pump the NO containing gas or material to the patient. One embodiment of such a system is shown as a 3-way valve in FIG. 12B.

The membrane and/or valve system may be combined with any of the other pneumatic configurations described above.

Manufacturing of Multi-Lumen Nasal Cannulas

As described above, the individual lumen of a multi-lumen cannula may be separately manufactured and then affixed to each other, or the multiple lumina can be extruded through a single die producing a multi-lumen tube.

Figure 16:
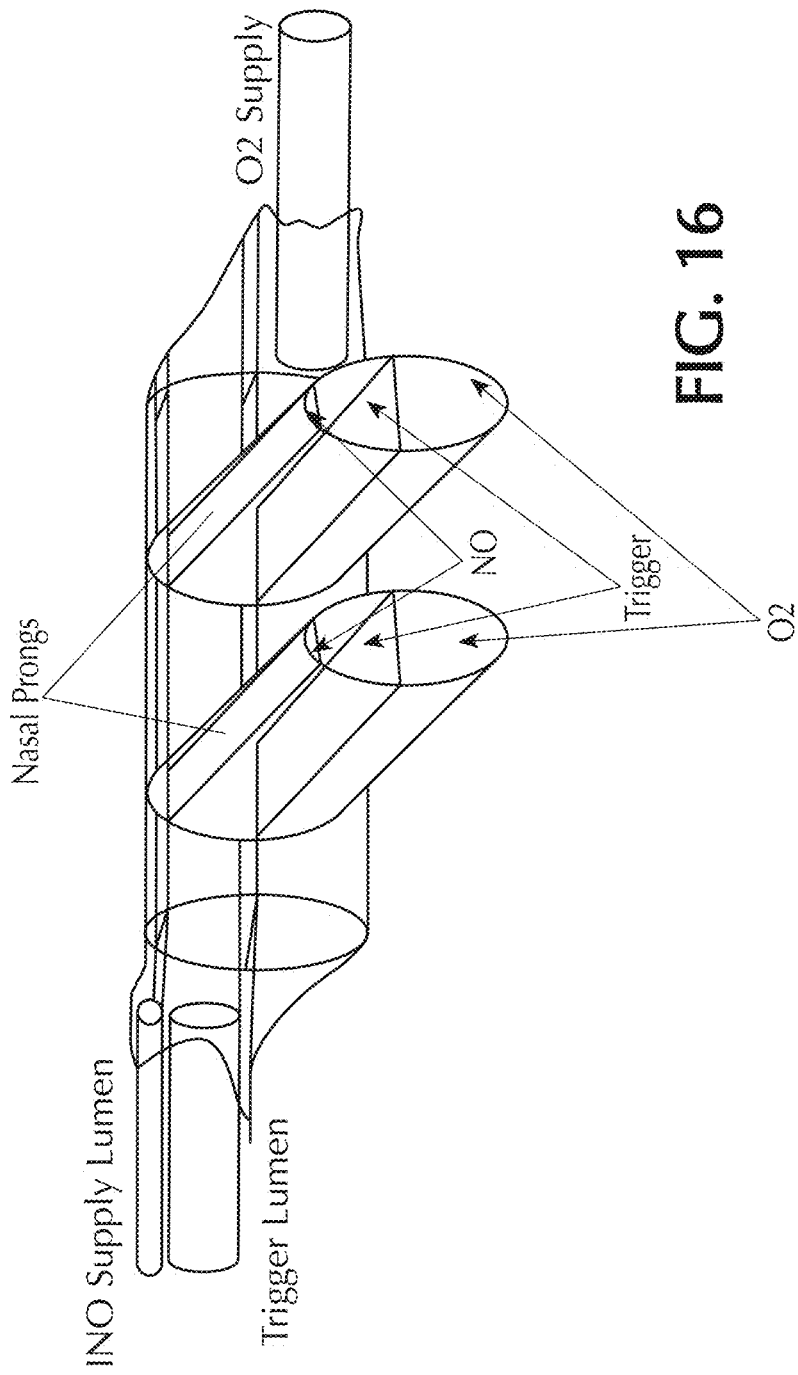
FIG. 16 shows a nasal cannula with a triple lumen nosepiece.

According to one or more embodiments, the multi-lumen nosepiece of the multi-lumen cannulas described herein may be manufactured by the following molding technique. For example, the cannula may have a triple lumen cannula nosepiece for separate oxygen, nitric oxide and triggering lumina. In one or more embodiments, the design of the nosepiece for the triple lumen cannula involves three lumens, two with inner diameters of approximately 0.080" (for oxygen and triggering) and one with a smaller inner diameter of approximately 0.045" (for nitric oxide) as shown in FIG. 16. However, this configuration may not be readily molded by typical injection molding techniques as the small lumen would require an injector pin (of outer diameter 0.045") which is too small to be robust in a molding tool designed to last for many uses, such as a million or more shots.

Figure 17:
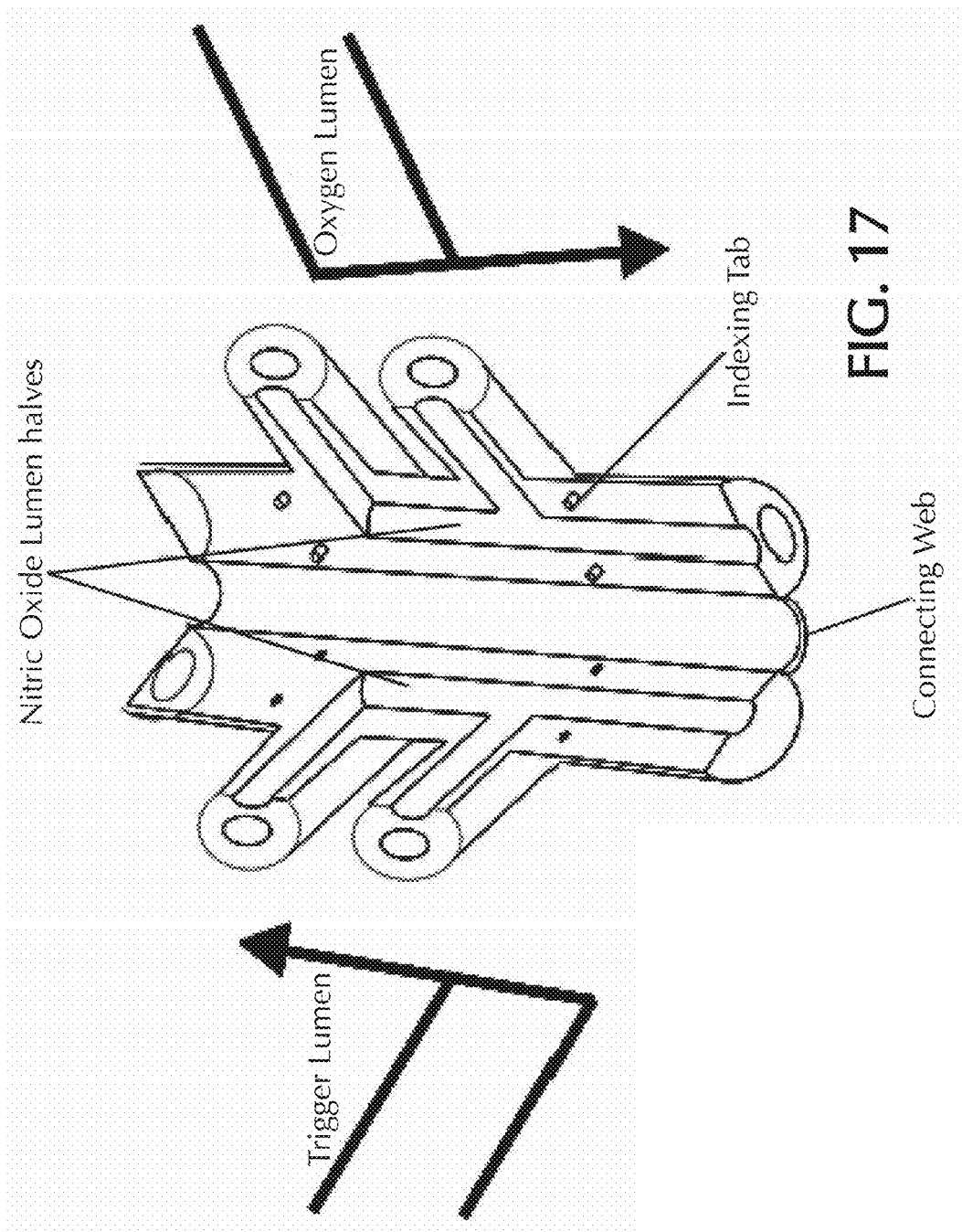
FIG. 17 shows a molded triple lumen nosepiece prior to assembly.
Figure 18:
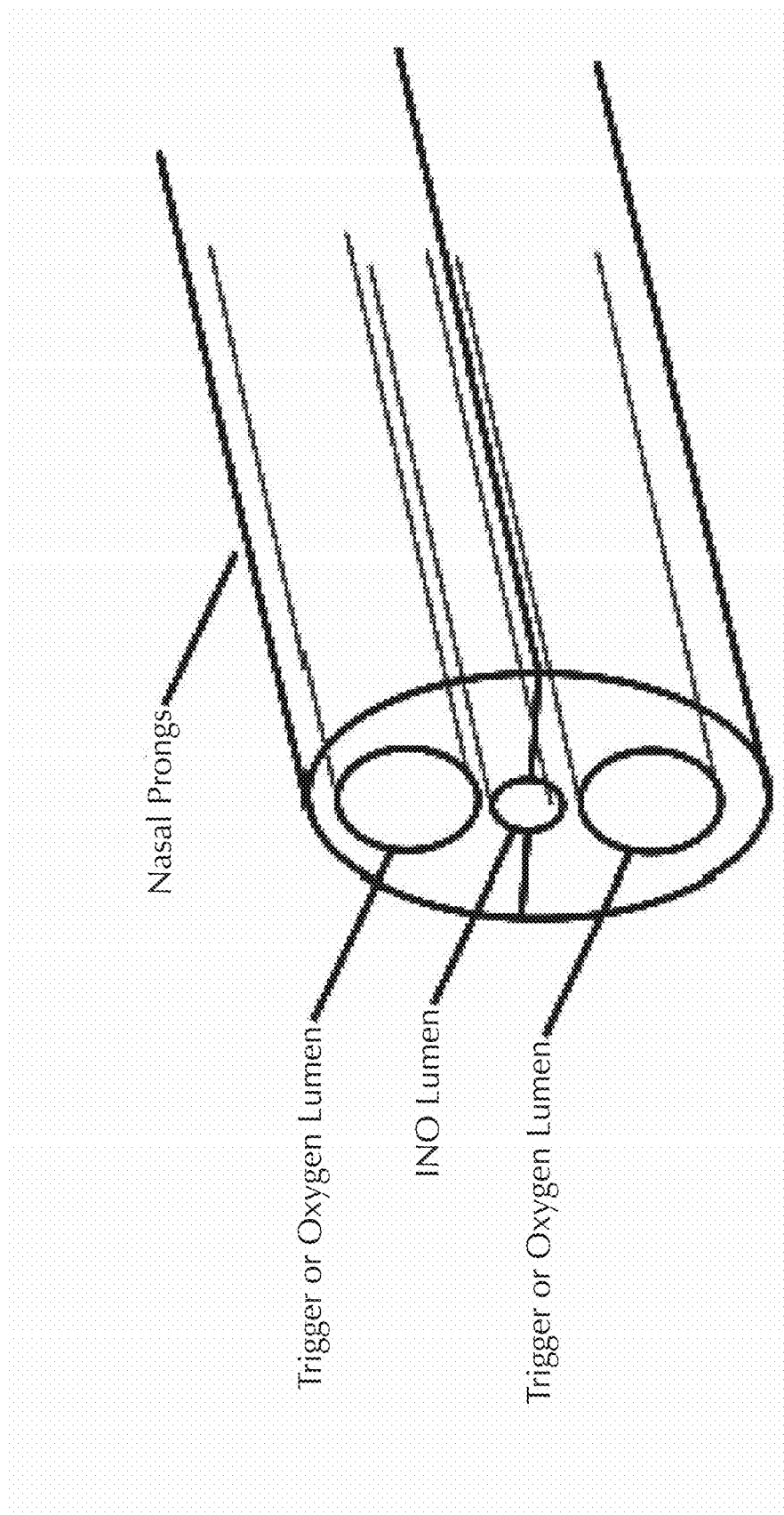
FIG. 18 shows the nasal prong of the assembled molded triple lumen nosepiece.

Accordingly, one approach to manufacture the multi-lumen cannula nosepiece is to mold two halves in urethane, PVC, silicone or other low durometer elastomer with the internals of the large lumen defined by larger injector pins (outer diameter 0.080") and with small half lumen indents defining the outline of the small lumen. These two halves would then be folded and bonded together, preferably with a bonding technique which does not produce residue or flash such as RF welding, to form a whole nosepiece. FIG. 17 shows one embodiment to circumvent the injector pin limitation with the small ID lumen being defined by indents in the halves, the two halves would be molded flat in one shot with a webbing holding the halves together and providing gross alignment during the folding and bonding process. Optionally, the molded halves may comprise integral holes and mating cylindrical tabs or other complementary members so that the halves will be properly aligned when they are folded together. The webbing may also be optional if appropriate complementary indexing members on the two halves ensure that the two portions forming the outer wall of the NO lumen will be properly aligned. The assembled nosepiece allows for three lumen inputs and tee's each lumen input within the internals of the nosepiece proper. FIG. 18 shows a perspective view of the nasal prong of the multi-lumen cannula nosepiece of FIG. 17 after the two halves have been assembled.

Again, the lumen ID may be adjusted as described in the previous sections. For example, the ID of the oxygen lumen may range from 0.05 to 0.12", the ID of the trigger lumen may range from 0.05 to 0.12", and the ID of the NO lumen may range from 0.01 to 0.08". In some embodiments, the IDs of the oxygen lumen and the trigger lumen may both be in the range from 0.07" to 0.09" (such as about 0.08") and the ID of the NO lumen may be in the range from 0.035 to 0.055" (such as about 0.045").

Figure 19:
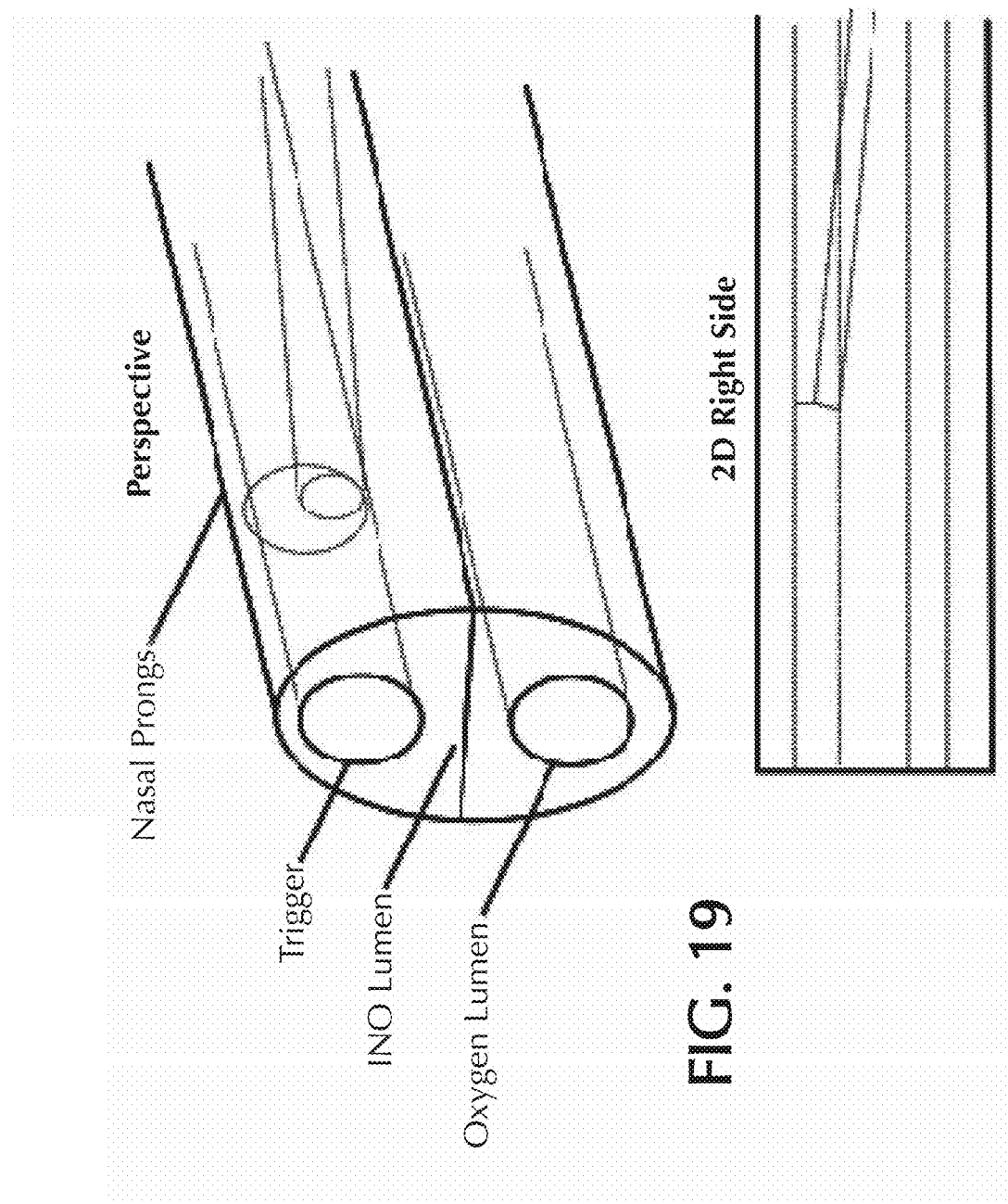
FIG. 19 shows a perspective and a two-dimensional representation of a nasal prong with a NO lumen proximal to and within a trigger lumen.

An alternate embodiment shown in FIG. 19 involves ensuring that the small NO lumen exits proximal to and within the larger trigger lumen. This embodiment ensures that any tip blockage of the larger trigger lumen (for which there is not a purge capability) would be blown out by the function of the NO pulse. The geometry of this embodiment must be carefully modeled to ensure that all NO in the larger trigger lumen reaches the respiratory system during inspiration and is not left behind to be swept out during exhalation.

Methods of Treatment

Any of the nasal cannulas described herein may be used in nitric oxide therapy to treat appropriate diseases. For example, the cannulas may be for pulsed NO therapy to treat chronic obstructive pulmonary disease (COPD) or pulmonary arterial hypertension (PAH). For these diseases, the delivery of the appropriate dose amounts and appropriate dose timing may be very important. For COPD, the NO may need to be pulsed early in inspiration, such as the first half of inspiration. If NO is not delivered in the right amount or at the right time, reversal of hypoxic vasoconstriction may occur, which would worsen the patient's condition. Furthermore, the dose amount may be very important for PAH because sudden discontinuation of therapy can lead to serious events such as rebound hypertension. Thus, significant dilution of the NO dose should be minimized for these diseases. Any of the cannula materials, configurations or methods described herein may be used to minimize dilution of the NO dose during NO therapy.

Examples

Figure 8:
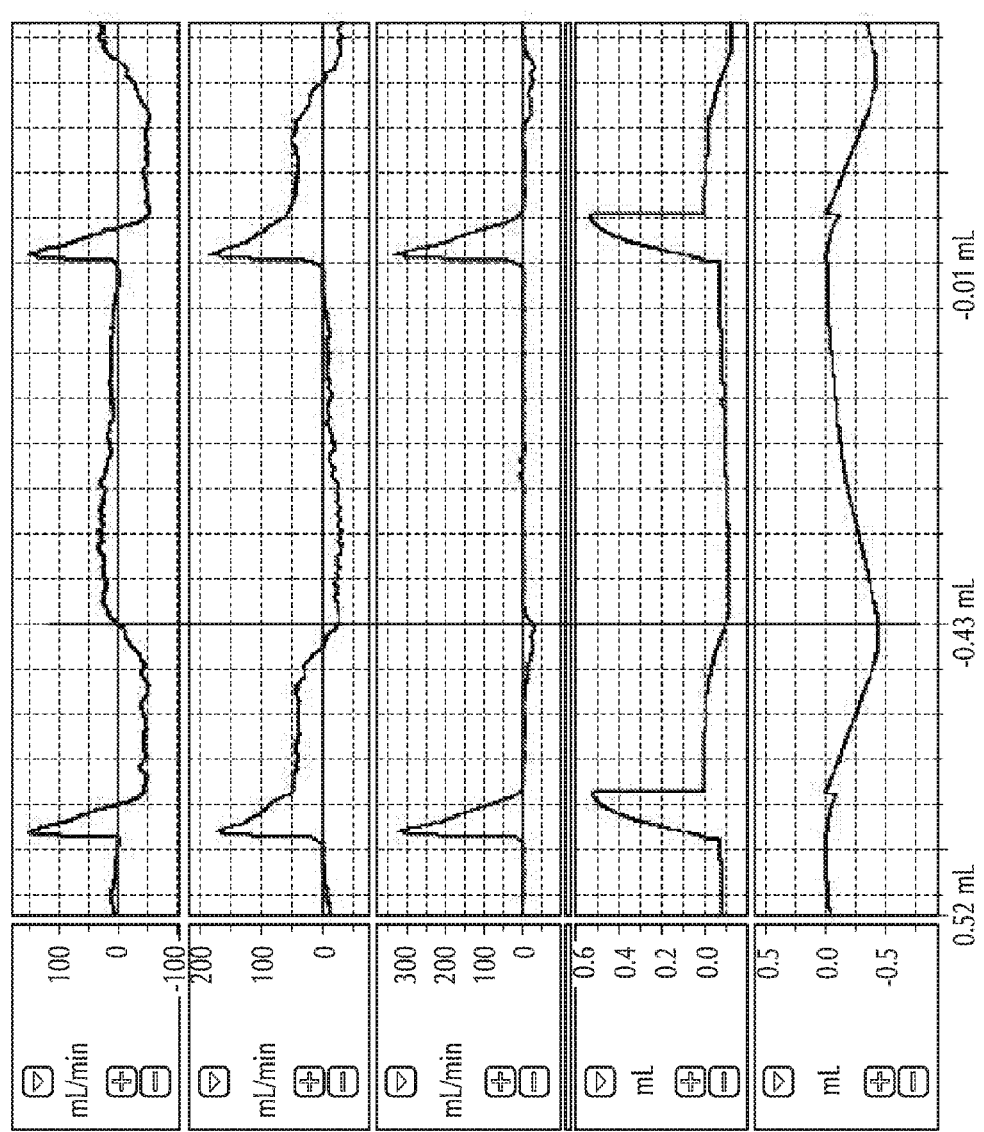
FIG. 8 shows retrograde flow during inspiratory breathing along with pulsed delivery.
Figure 9:
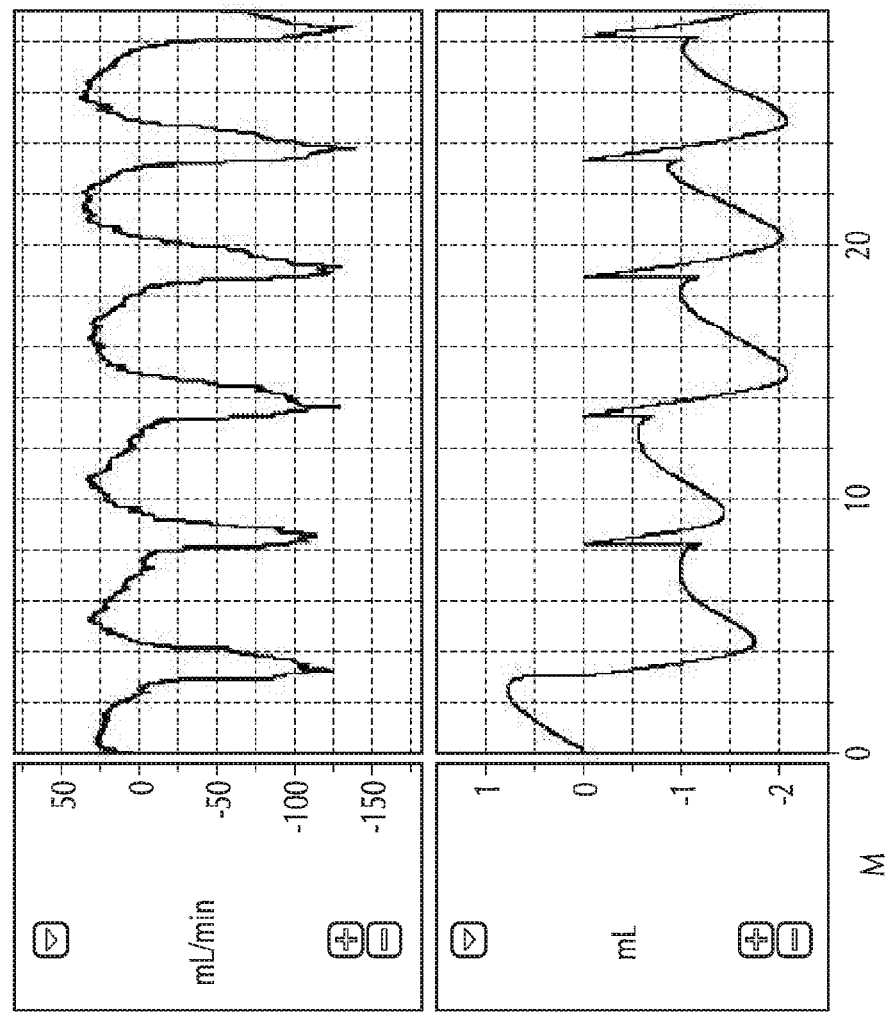
FIG. 9 shows retrograde flow during both inspiratory and expiratory breathing.

FIG. 8 shows an example of retrograde flow during inspiratory breath along with pulsed delivery. FIG. 9 shows an example of retrograde flow during both inspiratory and expiratory breath.

Figure 14:
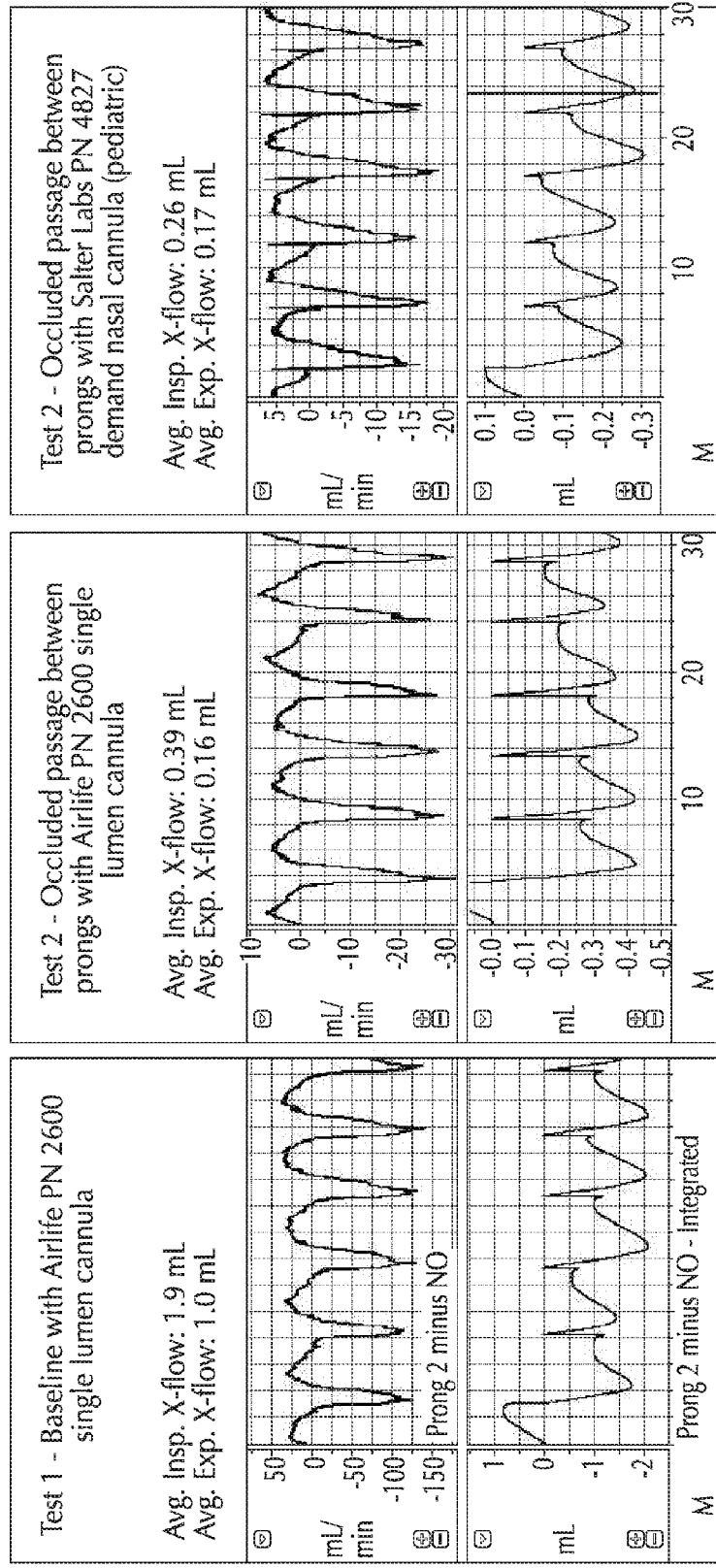
FIG. 14 shows retrograde flow for various cannula configurations.
Figure 15:
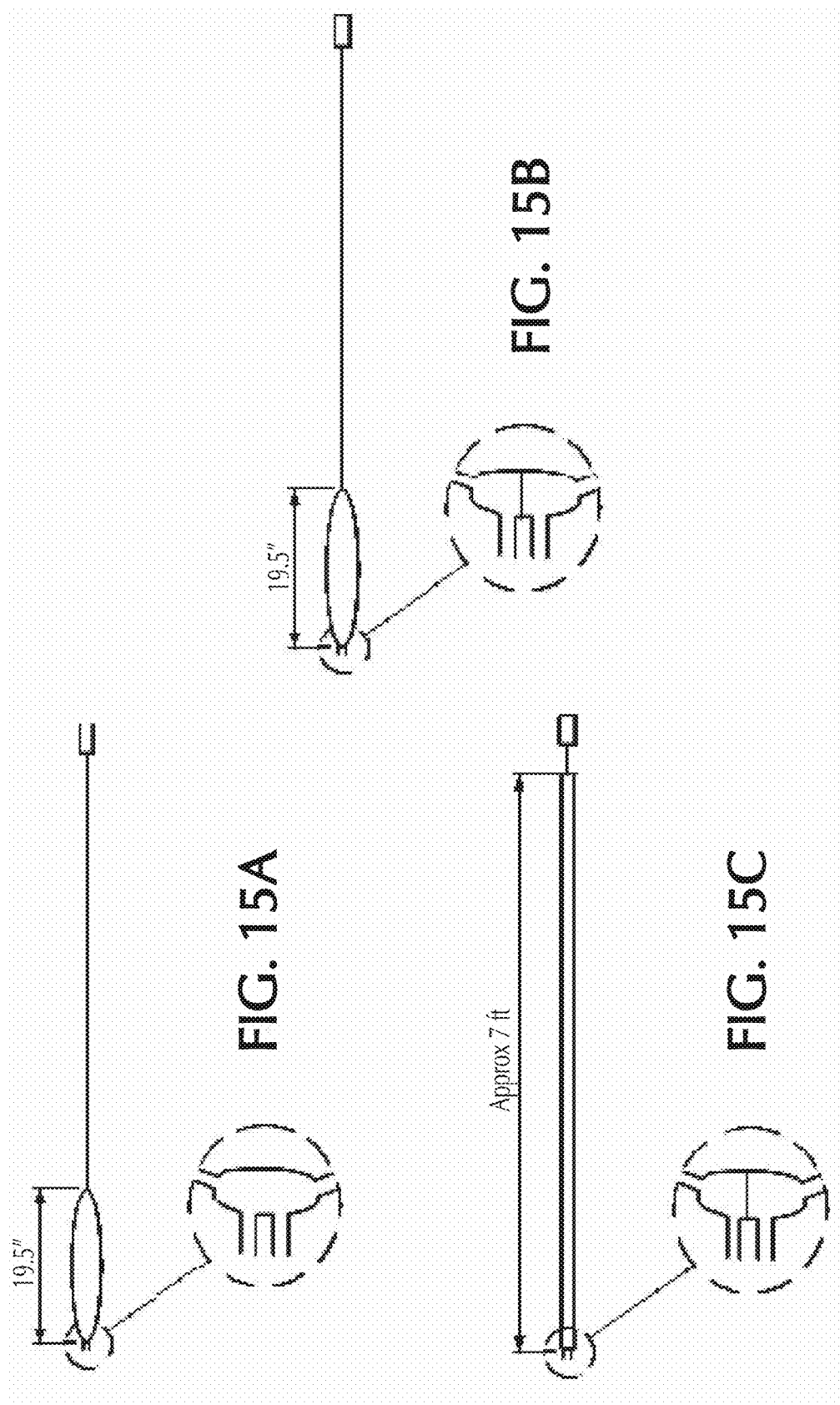
FIGS. 15A-C show the cannula configurations for Tests 1-3 of FIG. 14.

The retrograde flow for various nasal cannula configurations was tested. Typical nasal cannulas that deliver to both nares result in significant retrograde flow as shown in Test 1 of FIG. 14. The nasal cannula configuration of Test 1 is shown in FIG. 15A. For Test 2, the interconnect between the two prongs was occluded to increase the distance between the prongs to approximately 19 inches in the hopes that would eliminate the retrograde flow. The nasal cannula configuration of Test 2 is shown in FIG. 15B. As shown in Test 2 of FIG. 14, while the total volume of retrograde flow could be reduced, it was not eliminated. Further occluding the pathway with a 7 foot distance between the prongs, as shown in FIG. 15C, had minimal further impact, as shown in Test 3 of FIG. 14. Surprisingly, it was found that the only way tested that completely eliminated the retrograde flow was when separate circuits were used for the NO delivery to each nare.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A nasal cannula for therapeutic gas delivered to a patient, comprising:
    a nitric oxide source;
    an oxygen source;
    a first lumen, a second lumen, and a third lumen:
        the first lumen being a first therapeutic gas lumen for delivering a first therapeutic gas comprising nitric oxide from the nitric oxide source to the patient,
        the second lumen being a triggering lumen, and
        the third lumen being a second therapeutic gas lumen for delivering a second therapeutic gas comprising oxygen from the oxygen source to the patient; and
    a cannula nosepiece allowing separate flow paths to the patient for each of (i) the first therapeutic gas lumen, (ii) the triggering lumen, and (iii) the second therapeutic gas lumen; and
    wherein the cannula nosepiece comprises a nitric oxide flow path having an inner diameter that is smaller than an inner diameter of the first therapeutic gas lumen.

2. The nasal cannula of claim 1, wherein the nasal cannula one or more of (i) reduces dilution of one or more of the first and second therapeutic gases delivered to the patient and (ii) is configured to be placed in fluid communication with at least one system to deliver one or more of the first and second therapeutic gases to the patient.

3. The nasal cannula of claim 1, wherein the nasal cannula delivers one or more of the first and second therapeutic gases to the patient for treatment of one or more of chronic obstructive pulmonary disease (COPD) and pulmonary arterial hypertension (PAH).

4. The nasal cannula of claim 1, wherein the first therapeutic gas is nitric oxide and the second therapeutic gas is oxygen, and wherein the first therapeutic gas lumen for delivering nitric oxide is smaller than both of the second therapeutic gas lumen for delivering oxygen and the triggering lumen.

5. The nasal cannula of claim 1, wherein one or more of (i) the first therapeutic gas is nitric oxide and the first therapeutic gas lumen for delivering nitric oxide has an inner diameter of about 0.01 inches to about 0.08 inches and (ii) the triggering lumen has an inner diameter of about 0.05 inches to about 0.12 inches.

6. The nasal cannula of claim 1, wherein the nasal cannula is further comprising one or more of (i) a wall material having a low oxygen diffusion coefficient and (ii) at least one valve in fluid communication with the first therapeutic gas lumen.

7. The nasal cannula of claim 1, wherein the cannula is further comprising a fourth lumen:
    the fourth lumen being another first therapeutic gas lumen for delivering the first therapeutic gas to the patient; and
    wherein the first lumen is adapted to deliver the first therapeutic gas to one nostril of the patient and the fourth lumen is adapted to deliver the first therapeutic gas to another nostril of the patient.

8. A nasal cannula for therapeutic gas delivered to a patient, comprising:
    a nitric oxide source;
    an oxygen source;
    a first lumen and a second lumen:
        the first lumen being a combined first therapeutic gas and triggering lumen for both delivering a first therapeutic gas comprising nitric oxide from the nitric oxide source to the patient and triggering, and
        the second lumen being a second therapeutic gas lumen for delivering a second therapeutic gas comprising oxygen from the oxygen source to the patient,
        the combined first therapeutic gas and triggering lumen having an inner diameter that is smaller than an inner diameter of the second therapeutic gas lumen; and
    a cannula nosepiece allowing separate flow paths to the patient for each of (i) the combined first therapeutic gas and triggering lumen and (ii) the second therapeutic gas lumen; and
    wherein the cannula nosepiece comprises a nitric oxide flow path having an inner diameter that is smaller than an inner diameter of the combined first therapeutic gas and triggering lumen.

9. The nasal cannula of claim 8, wherein the nasal cannula one or more of (i) reduces dilution of one or more of the first and second therapeutic gases delivered to the patient and (ii) is configured to be placed in fluid communication with at least one system to deliver one or more of the first and second therapeutic gases to the patient.

10. The nasal cannula of claim 8, wherein the nasal cannula delivers one or more of the first and second therapeutic gases to the patient for treatment of one or more of chronic obstructive pulmonary disease (COPD) and pulmonary arterial hypertension (PAH).

11. The nasal cannula of claim 8, wherein one or more of (i) the first therapeutic gas is nitric oxide and the combined first therapeutic gas and triggering lumen has an inner diameter of about 0.01 inches to about 0.08 inches and (ii) the first therapeutic gas is nitric oxide and the cannula nosepiece comprises a combined nitric oxide and triggering flow path having an inner diameter that is smaller than an inner diameter of the combined first therapeutic gas and triggering lumen.

12. The nasal cannula of claim 8, wherein the nasal cannula is further comprising one or more of (i) a wall material having a low oxygen diffusion coefficient and (ii) at least one valve in fluid communication with the first therapeutic gas lumen.

13. A method of administering nitric oxide for treating pulmonary hypertension, the method comprising:
   administering a pulse of a gas comprising nitric oxide to a patient, wherein the pulse is administered through a nasal cannula comprising:
      a first lumen, a second lumen, and a third lumen:
         the first lumen being a first therapeutic gas lumen which delivers a gas comprising nitric oxide to the patient,
         the second lumen being a triggering lumen, and
         the third lumen being a second therapeutic gas lumen which delivers a gas comprising oxygen to the patient; and
      a cannula nosepiece allowing separate flow paths to the patient for each of (i) the first therapeutic gas lumen, (ii) the triggering lumen, and (iii) the second therapeutic gas lumen; and
   wherein the cannula nosepiece comprises a nitric oxide flow path having an inner diameter that is smaller than an inner diameter of the first therapeutic gas lumen.

14. The method of claim 13, wherein the nasal cannula one or more of (i) reduces dilution of one or more of the first and second therapeutic gases delivered to the patient and (ii) is configured to be placed in fluid communication with at least one system to deliver one or more of the first and second therapeutic gases to the patient.

15. The method of claim 13, wherein the nitric oxide flow path of the cannula nosepiece has a volume that is less than 10% of the volume of the pulse of the gas comprising nitric oxide.

16. The method of claim 13, wherein the nasal cannula comprises one or more of (i) a wall material having a low oxygen diffusion coefficient and (ii) at least one valve in fluid communication with the first therapeutic gas lumen.

17. The method of claim 13, wherein the nasal cannula is further comprising a fourth lumen:
   the fourth lumen being another first therapeutic gas lumen for delivering nitric oxide gas to the patient; and
   wherein the first lumen delivers nitric oxide gas to one nostril of the patient and the fourth lumen delivers nitric oxide gas to another nostril of the patient.

18. A method of administering nitric oxide for treating pulmonary hypertension, the method comprising:
   administering a pulse of a gas comprising nitric oxide to a patient, wherein the pulse is administered through a nasal cannula comprising:
      a first lumen and a second lumen:
         the first lumen being a combined first therapeutic gas and triggering lumen which both delivers a gas comprising nitric oxide to the patient and triggers, and
         the second lumen being a second therapeutic gas lumen which delivers a gas comprising oxygen to the patient; and
      a cannula nosepiece allowing separate flow paths to the patient for each of (i) the combined first therapeutic gas and triggering lumen and (ii) the second therapeutic gas lumen; and
   wherein the cannula nosepiece comprising a nitric oxide flow path having an inner diameter that is smaller than an inner diameter of the combined first therapeutic gas and triggering lumen.

19. The method of claim 18, wherein the nasal cannula one or more of (i) reduces dilution of one or more of the first and second therapeutic gases delivered to the patient and (ii) is configured to be placed in fluid communication with at least one system to deliver one or more of the first and second therapeutic gases to the patient.

20. The method of claim 18, wherein the nitric oxide flow path of the cannula nosepiece has a volume that is less than 10% of the volume of the pulse of the gas comprising nitric oxide.

21. The method of claim 18, wherein the nasal cannula comprises one or more of (i) a wall material having a low oxygen diffusion coefficient and (ii) at least one valve in fluid communication with the first therapeutic gas lumen.

* * * * *

UNITED STATES PATENT AND TRADEMARK OFFICE
CERTIFICATE OF CORRECTION

PATENT NO. : 9,795,756 B2  
APPLICATION NO. : 14/096548  
DATED : October 24, 2017  
INVENTOR(S) : Flanagan et al.

Page 1 of 1

It is certified that error appears in the above-identified patent and that said Letters Patent is hereby corrected as shown below:

In Column 12, Line 23, Claim 7, Line 1, before "cannula" insert -- nasal --, therefor.

Signed and Sealed this
Fifteenth Day of May, 2018

Andrei Iancu
*Director of the United States Patent and Trademark Office*